United States Patent [19]

Sanfilippo et al.

[11] Patent Number: 5,342,851
[45] Date of Patent: Aug. 30, 1994

[54] SUBSTITUTED THIAZOLE DERIVATIVES USEFUL AS PLATELET AGGREGATION INHIBITORS

[75] Inventors: Pauline J. Sanfilippo, Chester Springs, Pa.; Maud Urbanski, Belle Mead, N.J.; John R. Carson, Norristown; Richard J. Carmosin, Quakertown, both of Pa.

[73] Assignee: McNeil-PPC, Inc., Milltown, N.J.

[21] Appl. No.: 958,193

[22] Filed: Oct. 7, 1992

[51] Int. Cl.$^5$ .................. C07D 417/04; A61K 31/425
[52] U.S. Cl. ..................... 514/370; 514/326; 546/209; 548/194; 548/204
[58] Field of Search .............. 548/194; 546/209; 514/370, 326

[56] References Cited

PUBLICATIONS

Singh, Indian J. Chem. Sect B. 29B(4) 342,(1990).

Primary Examiner—Robert Gerstl
Attorney, Agent, or Firm—Joseph J. Brindisi

[57] ABSTRACT

This invention relates to substituted thiazole derivatives of the following general formula, the substituent groups of which are as defined herein:

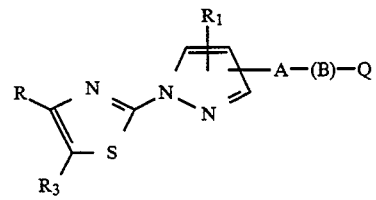

I

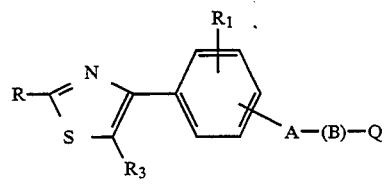

II

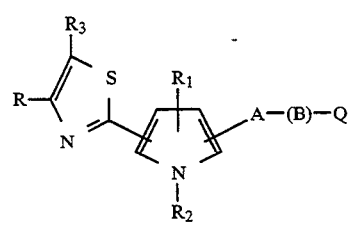

III

These compounds are useful as inhibitors of platelet aggregation and inhibitors of adhesion molecules and may be provided in pharmaceutical compositions and in methods of treating reperfusion thrombosis injury in patients.

14 Claims, No Drawings

SUBSTITUTED THIAZOLE DERIVATIVES USEFUL AS PLATELET AGGREGATION INHIBITORS

FIELD OF THE INVENTION

This invention relates to substituted thiazole derivatives as described further below. These compounds are useful as inhibitors of platelet aggregation and inhibitors of adhesion molecules and may be provided in pharmaceutical compositions and in methods of treating reperfusion thrombosis injury in patients.

BACKGROUND OF THE INVENTION

The present invention provides novel thiazole compounds which are useful as inhibitors to platelet aggregation and adhesion molecules and novel intermediate compounds for producing such inhibitor compounds. The compounds of the invention are useful for treating reperfusion thrombosis injury in patients. Various thiazole derivatives have been identified which have biological activity. For example U.S. Pat. No. 4,791,200 discloses compounds of the formula:

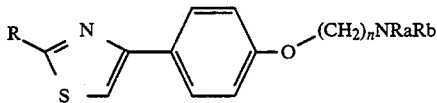

where R is H, alkyl, aryl or substituted phenyl and Ra and Rb are H, alkyl, aryl or substituted phenyl. These compounds are disclosed as antisecretory agents.

Chem. Pharm. Bull. 39 651–657 (1991) discloses compounds of the formula:

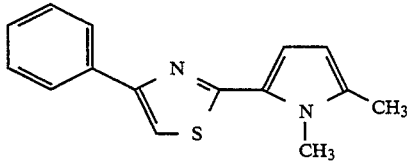

wherein diphenylimidazole and diphenyl thiazole derivatives are described as inhibitors of platelet aggregation via an arachidonic acid mechanism.

Arterial thrombosis is primarily responsible for acute myocardial infarction, unstable angina and thrombotic stroke while venous thrombosis is associated with pulmonary embolism and deep vein thrombosis. A dynamic balance exists between coagulation and fibrinolysis which are regulated by the enzymes thrombin and plasmin, respectively. Superimposed on this is the process of platelet aggregation and platelet adhesion to vessel walls. Inhibition of platelet aggregation is a means of treating thrombosis for reperfusion injury. The present invention focuses on new chemical compounds which demonstrate platelet aggregation inhibition.

It is therefore an object of the present invention to provide novel thiazole derivatives which are useful as platelet aggregation inhibitors and their methods of use. Additional objects and advantages of the invention will be set forth, in part, in the description which follows and in part will be obvious from this description, or may be learned by practice of the invention. The objects and advantages of the invention are realized and obtained by means of the methods, and the combinations particularly pointed out in the appended claims.

SUMMARY OF THE INVENTION

To achieve the objects in accordance with the purposes of the invention, as embodied and fully described herein the present invention relates to substituted thiazole derivatives of the following formulas:

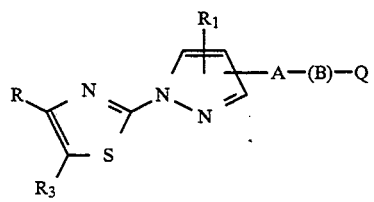

I

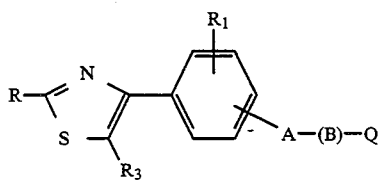

II

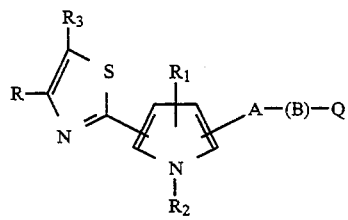

III wherein
R and $R_3$ are the same or different and are selected from hydrogen, hydroxy, carboxy, alkylcarboxy ($C_1$-$C_4$), alkyl ($C_1$-$C_8$), trifluoromethyl, halogen (such as bromo, chloro, iodo or fluoro), aryl and substituted aryl (preferably phenyl, naphthyl, substituted phenyl or naphthyl) where the aryl substituents are selected from the group consisting of cyano, nitro, trifluoromethyl, carboxy, amino, carboxamido, tosyl, halogen, alkyl ($C_1$-$C_4$), carboalkoxy ($C_1$-$C_4$), alkoxy ($C_1$-$C_4$), or heteroaryl wherein the heteroaryl contains 1–4 heteroatoms such as nitrogen and sulfur (preferably, thiophene, imidazole or pyridine) or R and $R_3$ may be taken together to form a ring (except for formula II) such as benzene or substituted benzene wherein the heteroaryl substituents are selected from the group consisting of cyano, nitro, trifluoromethyl, carboxy, amino, carboxamido, halogen, alkylcarboxy, alkyl or alkoxy;

$R_1$ is selected from the group consisting of halogen, hydrogen, hydroxy, carboxy, alkylcarboxy ($C_1$-$C_4$), alkyl ($C_1$-$C_5$), trifluoromethyl, aryl and substituted aryl (preferably phenyl, naphthyl, substituted phenyl or naphthyl) where the aryl substituents are as defined above for R and heterocycle ($C_3$-$C_6$) and substituted heterocycle (preferably, thiophene, imidazole or pyridine);

$R_2$ is hydrogen or alkyl ($C_1$-$C_5$);

A is selected from the group consisting of carbonyl, carboxyl, carboxamido, amido, oxymethyl, aminomethyl or methylene;

B is selected from alkyl ($C_1$-$C_9$), branched alkyl ($C_1$-$C_9$), phenyl or aralkyl ($C_1$-$C_5$);

Q is selected from hydroxy, alkoxy ($C_1-C_5$), halogen, cyano, carboxy, alkoxycarbonyl ($C_1-C_5$), or $NR_4R_5$, where $R_4$ and $R_5$ are independently selected from the group consisting of hydrogen, alkyl ($C_1-C_5$), cycloalkyl ($C_3-C_8$), or $NR_4R_5$ may be taken together to form a heterocyclic ring such as piperidine, pyrrolidine, pyrrolidinone, piperidinone, phthalimide, imidazole, piperazine, substituted piperazine or morpholine and their benzo fused analogues such as 2,6-dihydro-isoindole and benzimidazole and any N-oxides thereof such as 2-oxo-2,6-dihydro-isoindole or $NR_4R_5$ may be a guanidine, urea, thiourea, hydrazine, amidine, or substituted amidine wherein the substituents are selected from the group consisting of alkyl ($C_1-C_4$), hydroxyl and amino.

The present invention also includes pharmaceutically acceptable salts of the above-described compounds.

As embodied and fully described herein, the invention further comprises novel intermediate compounds for preparing the thiazole derivatives described above. These novel intermediate compounds have the formula:

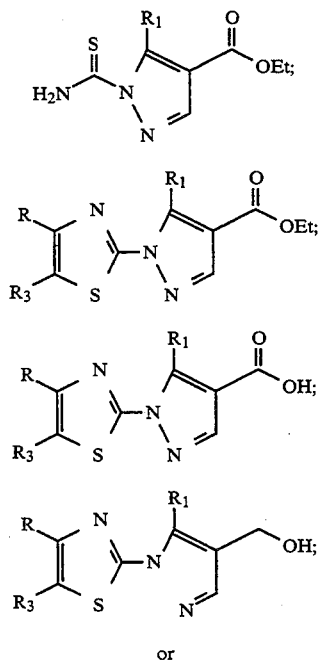

or wherein R, $R_1$, and $R_3$ are as defined above.

The substituted thiazole derivatives and their pharmaceutically acceptable salts are nonpeptidal adhesion molecule antagonists which inhibit platelet aggregation. The compounds of the invention can influence cell-cell and cell-matrix interactions and can inhibit the binding of fibrinogen to the fibrinogen receptor of blood platelets. In particular, the compounds of the invention prevent the formation of blood platelet thrombi and thus may be used to control or prevent illnesses such as thrombosis, stroke, unstable angina, cardiac infarct, inflammation and arteriosclerosis. The present invention thus provides for methods of treating reperfusion thrombosis injury in a patient comprising the step of administering to the plasma of a patient a platelet aggregation inhibiting effective amount of a compound as described above. The present invention also provides for pharmaceutical compositions comprising one or more compounds as described above and a pharmaceutically inert carrier.

It is to be understood that both the foregoing general description and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following examples section. The following provides the best mode presently contemplated for carrying out the present invention by disclosing the preferred compounds, compositions and methods of the invention.

In accordance with the invention novel compounds, compositions and methods are provided to achieve the objects in accordance with the purposes of the invention, as embodied and fully described herein. The invention relates to substituted thiazoles which have activity as adhesion molecule inhibitors which are useful as anticoagulants or anti-inflammatory agents. Several of the intermediates used in the synthesis of the target thiazoles are novel compounds and are considered to be part of the invention.

The substituted thiazoles of the invention are prepared as outlined in the following reaction schemes.

SCHEME 1

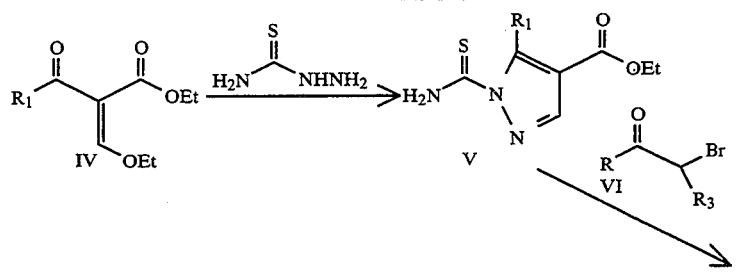

-continued
SCHEME 1
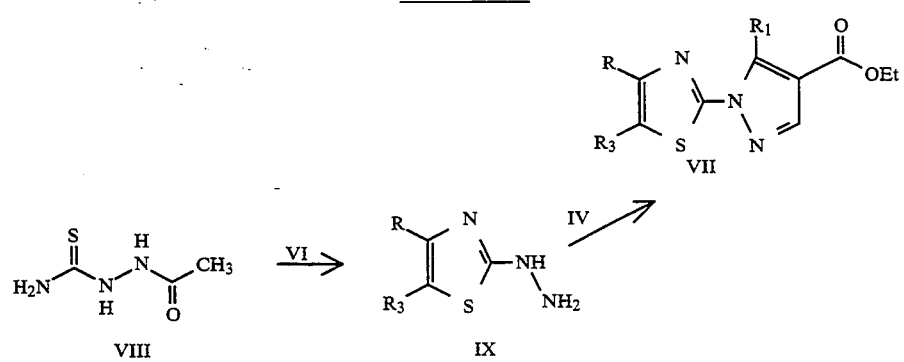
SCHEME 2
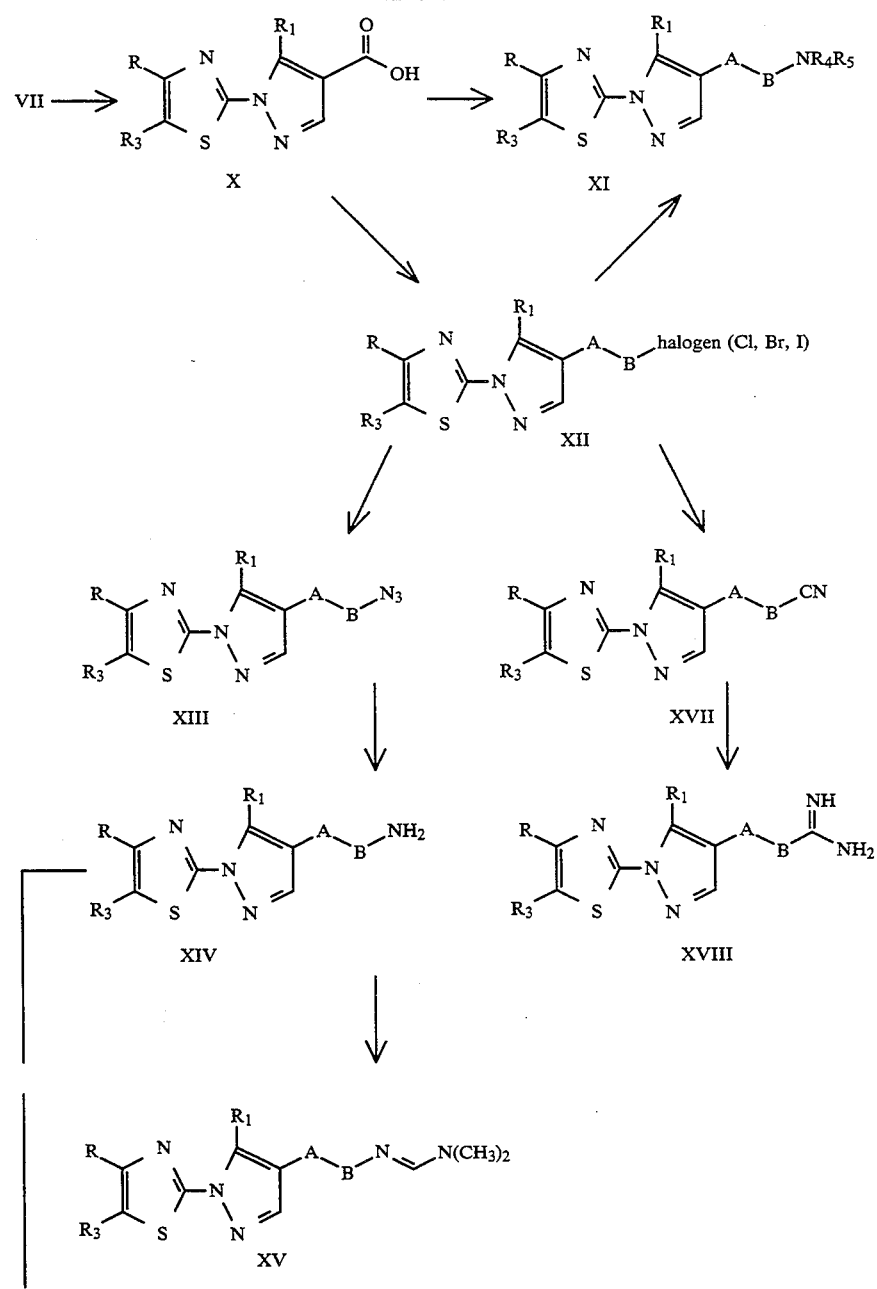

-continued
SCHEME 2
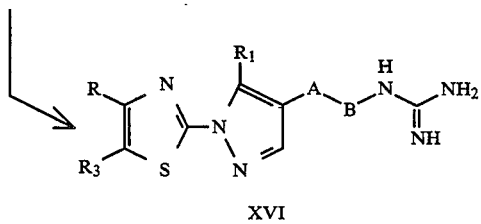
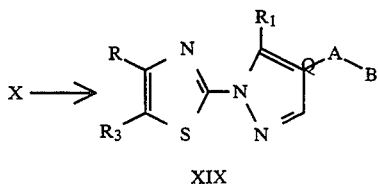
SCHEME 3
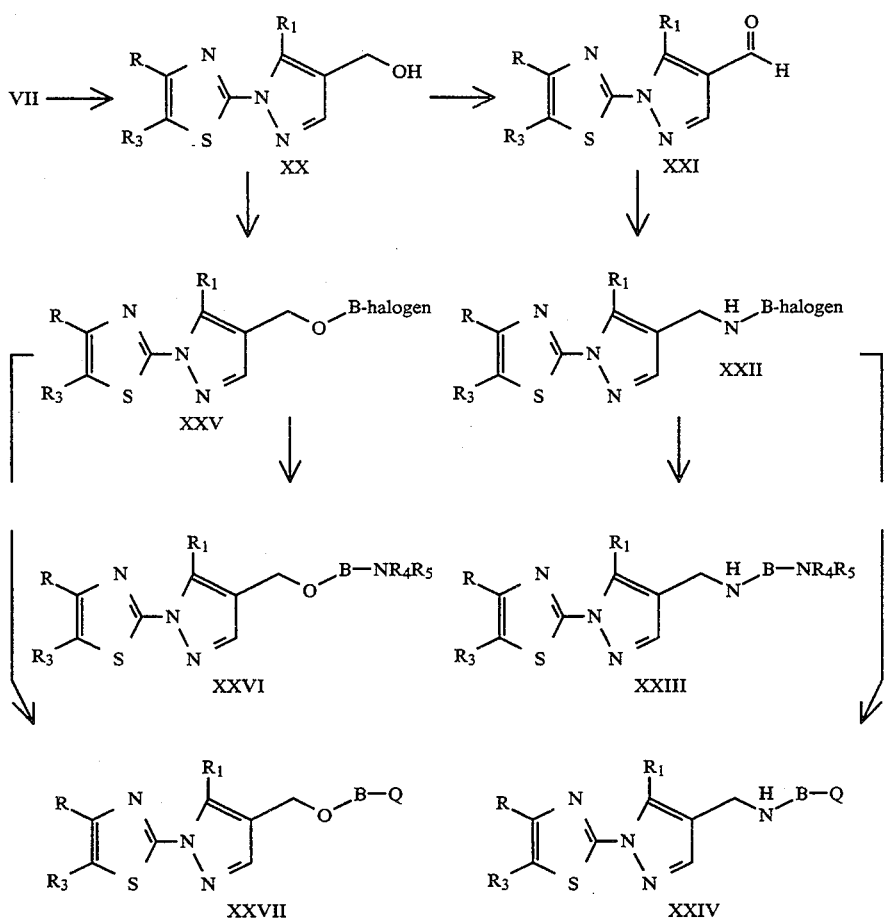
Q = CN, N₃, C(NH)NH₂,
NHC(NH)NH₂ and N(CH₂CH₃)₂

SCHEME 4
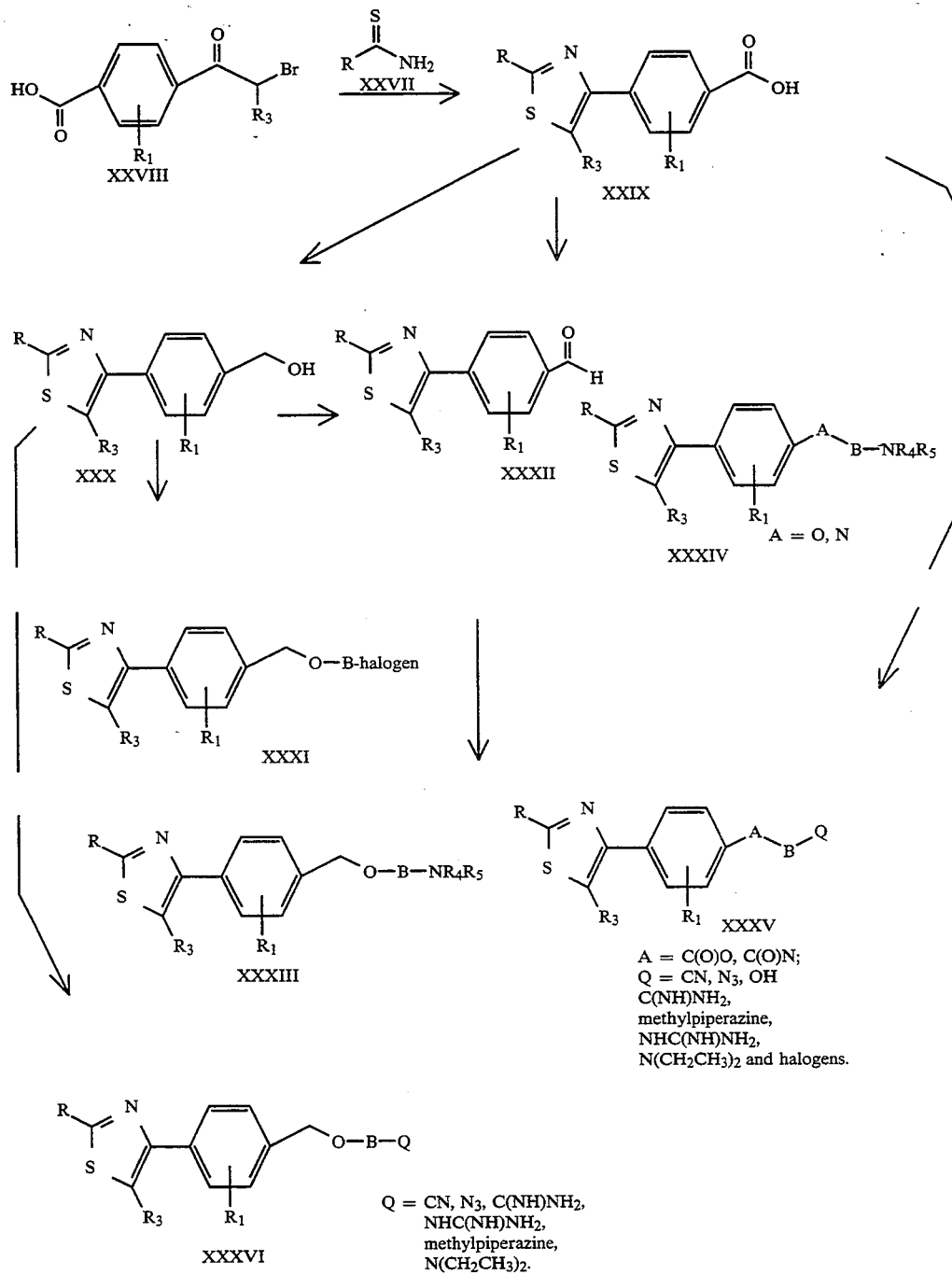
SCHEME 5
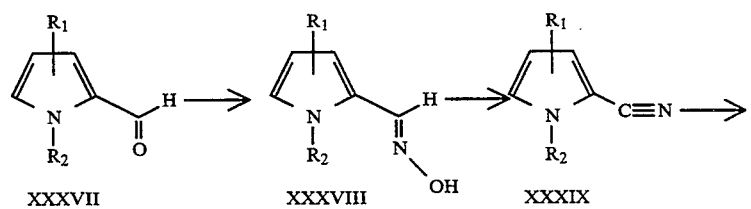

SCHEME 5

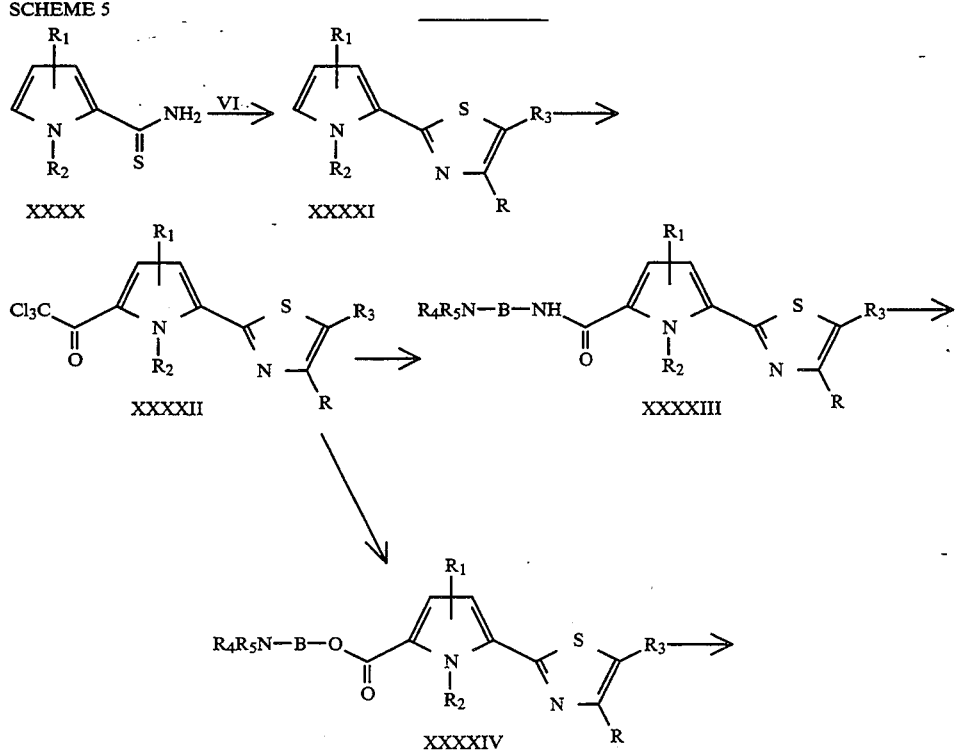

As can be seen from Scheme 1, treatment of the ethoxy propenoate derivative IV with thiosemicarbazide in a solvent such as acetone or ethanol, at −20° to 0° C. for 2–4 hours gives the thioamidopyrazole derivative V. Compound V can be reacted with an appropriately substituted phenacyl bromide VI in a suitable solvent such as acetone or ethanol, at room temperature to reflux for 1–4 hours to give the ester derivative VII.

Alternatively, the ester derivative VII may be prepared by treating 1-acetylthiosemicarbazide VIII with an appropriately substituted phenacylbromide VI, in a suitable solvent such as acetone or ethanol, at 0° to 60° C. for 2–6 hours; followed by hydrolysis of the intermediate acetylhydrazine derivative using aqueous acid such as 1–10N hydrochloric or sulfuric acid, at room temperature to reflux, for 1–48 hours to give the hydrazine derivative IX. Said hydrazine derivative IX can be reacted with an appropriately substituted ethoxy propenoate derivative IV, in a suitable solvent such as acetone or ethanol, at −20° to 0° C. for 2–6 hours to give the ester derivative VII.

As can be seen in Scheme 2, treatment of ester VII with an appropriate base, such as potassium hydroxide or sodium hydroxide, in a suitable alcoholic solvent such as ethanol at room temperature to reflux for 2–6 hours, produces the corresponding acid derivative X.

The acid derivative X can be treated with a number of reactants to give all of the compounds represented in Scheme 2. The treatment of acid X with a substituted diamine and an appropriate coupling agent, such as dicyclohexylcarbodiimide or carbonyldiimidazole in a suitable solvent such as dimethyl sulfoxide (DMSO), N,N-dimethylformamide (DMF) or methylene chloride at room temperature to 60° C. for 6–72 hours gives amide XI (A=C(O)NH).

Alternatively, acid X can be treated with a halogenated alkylamine and an appropriate coupling agent, such as dicyclohexylcarbodiimide or carbonyldiimidazole in a suitable solvent such as DMSO, DMF or methylene chloride, at room temperature to 60° C. for 6–72 hours to give the halide derivative XII (A=C(O)NH). Treatment of compound XII (A=C(O)NH) with any appropriate nucleophile, such as an amine, in the presence or absence of a suitable solvent such as DMF, at room temperature to 60° C. for 6–72 hours gives the amide (A=C(O)NH) XI.

Treatment of XII (A=C(O)NH) with sodium azide in a suitable solvent such as DMSO or DMF, at room temperature to 100° C. for 1–6 hours gives an azide derivative XIII (A=C(O)NH). Compound XIII (A=C(O)NH) may be treated with a suitable reducing agent such as lithium aluminum hydride, triphenylphosphine, zinc, iron or sodium borohydride in an appropriate solvent such as ether, acetone, toluene or an aliphatic alcohol, at 0° to 100° C. to give the amino derivative XIV (A=C(O)NH).

The amino derivative XIV (A=C(O)NH) can be treated with DMF-dimethyl acetal, at reflux for 4–6 hours to give the amidine derivative XV (A=C(O)NH). Alternatively, the amino derivative XIV (A=C(O)NH) can be treated with 1-guanyl-3,5-dimethyl-pyrazole nitrate (Can. J. Chem. 36, 1541, 1958) and triethylamine in a suitable solvent, such as DMF at room temperature to 80° C. for 3–6 hours to give the guanidine derivative XVI (A=C(O)NH).

Compound XII (A=C(O)NH) may also be treated with a cyanide source such as sodium cyanide or potassium cyanide in a suitable solvent such as DMF, DMSO or methylene chloride from 0° to 60° C. to give the cyano derivative XVII (A=C(O)NH). Treatment of the cyano derivative XVII with hydrogen sulfide, thioacetamide or hydrogen chloride gas in a suitable solvent such as toluene, DMF or ethanol; followed by treatment with ammonium acetate, ammonium chloride or ammonia to give the amidine derivative XVIII (A=C(O)NH).

The acid derivative X may also be treated with a substituted amino-alcohol and an appropriate coupling agent such as dicyclohexylcarbodiimide or carbonyldiimidazole in a suitable solvent such as DMSO, DMF or methylene chloride at room temperature to 60° C. for 6-72 hours to give the ester derivative XI (A=C(O)O). Likewise, treatment of the acid derivative X with an appropriate halogenated alcohol in the presence or absence of a suitable solvent such as DMF, at room temperature to 60° C. for 6-72 hours gives the haloderivative XII (A=C(O)O). Treatment of XII (A=C(O)O) with an appropriate nucleophile such as an amine, in a suitable solvent such as DMF or neat, at room temperature to 60° C. for 6-72 hours gives the ester derivative XI (A=C(O)O). The acid derivative X may also be treated with a primary amino-alcohol and an appropriate coupling agent such as dicyclohexylcarbodiimide or carbonyldiimidazole in a suitable solvent such as DMSO, DMF or methylene chloride at room temperature to 60° C. for 6-72 hours to give the amide derivative XIX (A=C(O)NH, Q=OH).

Following Scheme 3, ester VII can be treated with a suitable reducing agent such as borane/tetrahydrofuran, in an appropriate solvent such as tetrahydrofuran (THF) at 0° C. to reflux for 4-10 hours to give the alcohol derivative XX. Alcohol XX may be oxidized with a suitable agent such as pyridinium chlorochromate, pyridinium dichromate or potassium permanganate in an appropriate solvent such as methylene chloride or THF at 0° to 40° C. for 2-6 hours to give the aldehyde derivative XXI. Treatment of said aldehyde with sodium cyanoborohydride and a suitable halogenated alkylamine, in an alcoholic solvent such as methanol, at 020 0 to 40° C., for 8-16 hours gives the halo derivative XXII. Compound XXII may be treated with a suitable amine in an appropriate solvent such as DMF at room temperature for 8-72 hours to give the substituted amine derivative XXIII.

Compound XXII may be treated with the same conditions outlined for Compound XII to give the substituted derivative XXIV; where the identity of the substituent group Q is determined by the reaction conditions.

Alternatively, alcohol XX may be treated with an appropriate chloroalkylbromide and a base such as potassium carbonate, potassium hydroxide or NaH in a suitable solvent such as DMF, ethanol or THF to give an ether derivative XXV. Compound XXV may be treated with an appropriate amine in the presence or absence of a suitable solvent such as DMF, at room temperature to reflux for 1-16 hours to give the aminoether derivative XXVI. Alternatively the amino ether derivative XXVI can be prepared directly from the alcohol XX. The treatment of said alcohol with a suitable disubstituted aminoalkylhalide and an appropriate base such as potassium carbonate, potassium hydroxide or NaH in a suitable solvent such as DMF, ethanol or THF gives the aminoether derivative XXVI.

Compound XXV may be treated with the same conditions outlined for Compound XII to give the substituted derivative XXVII; where the identity of the substituent group Q is determined by the reaction conditions.

As can be seen in Scheme 4, thioamides (prepared by the treatment of known amides with any suitable sulfur source such as Lawesson's reagent or phosphorous pentasulfide), can be treated with an appropriately substituted phenacylbromide derivative XXVIII in a suitable solvent such as acetone or ethanol, at room temperature to reflux for 1-6 hours; to give the acid derivative XXIX.

Acid XXIX can be treated with the same conditions that were previously outlined for thiazole pyrazole acid derivative X to give the thiazole-phenyl derivatives XXX, XXXI, XXXII, XXXIII, XXIV, XXXV and XXXVI.

As can be seen in Scheme 5, the pyrrolecarboxaldehyde derivative XXXVII, can be treated with hydroxylamine hydrochloride and sodium acetate trihydrate in a suitable solvent such as water at room temperature for 4-6 hours to give the substituted oxime derivative XXXVIII. Treatment of compound XXXVIII with acetic anhydride at reflux for 1-2 hours gives the nitrile derivative XXXIX. Said nitrile may be treated with hydrogen sulfide and triethylamine in pyridine to give the thioamide derivative XXXX. Compound XXXX may be treated with an appropriate phenacylbromide VI, in a suitable solvent such as acetone or ethanol, at room temperature to reflux for 1-3 hours to give thiazole-pyrrole XXXXI. Treatment of the thiazole-pyrrole derivative XXXXI with trichloroacetylchloride in a suitable solvent, such as toluene gives the trichloroacetyl derivative XXXXII. Compound XXXXII may be treated with an appropriately substituted diamine in a suitable solvent such as acetonitrile or DMF at room temperature for 1-16 hours to give the amide derivative XXXXIII. Likewise, treatment of XXXXII with an appropriately substituted amino-alcohol in a suitable solvent such as acetonitrile or DMF at room temperature to 60° C. for 1-16 hours to give the ester derivative XXXXIV.

Treatment of the amide derivative XXXXIII where $NR_4R_5=NH_2$, with sodium cyanoborohydride and a suitable ketone such as cyclohexanone in an appropriate solvent such as methanol, at room temperature for 16 hours gives a substituted amide derivative XXXXIII where $NR_4R_5=NH$-cyclohexyl.

EXAMPLES

The invention will now be illustrated by examples. The examples are not intended to be limiting of the scope of the present invention. In conjunction with the detailed and general description above, the examples provide further understanding of the present invention and outline a process for producing the compounds of the invention.

The following examples represent preferred embodiments of the compounds, compositions, processes and methods of the invention for satisfying the stated objects of the invention.

Melting point determinations were carried out on a Thomas Hoover capillary melting point apparatus and are uncorrected. All compounds had spectra (Elemental Analysis, IR, $^1H$ NMR, MS) consistent with their assigned structures. The infrared spectra (IR) were recorded on a Perkin Elmer 1430 spectrometer and are expressed in reciprocal centimeters. Nuclear magnetic resonance (NMR) spectra for hydrogen atoms were measured in the indicated solvent with tetramethylsilane (TMS) as the internal standard on a Brucker WP-100 or a GE QE-300 spectrometer. The values are expressed in parts per million downfield from TMS. Elemental analyses were determined on a Perkin Elmer 2400 spectrometer and are expressed in percentage by weight of each element per total molecular weight and such found values are reported in the tables and are consistent with the assigned structures. The mass spectra (MS) were determined on a FINNIGAN MAT 8230 or a FINNIGAN MAT INCOS 50, single stage, quadrupole using desorption chemical ionization techniques. All column chromatography were run using Silica Gel 60, 230–400 mesh and any appropriate commercially available solvent. Unless otherwise noted, the materials used in the examples and substitutes therefor are obtained from readily available commercial suppliers or synthesized by standard methods known to anyone skilled in the art of chemical synthesis. The substituent groups, which vary between examples are assumed to be hydrogen unless otherwise noted.

EXAMPLE 1

1-Thio-[4-carboethoxy-5-trifluoromethylpyrazol-1-yl]amide

To a −15° C. solution containing thiosemicarbazide (34.4 g, 0.38M) in EtOH (500 mL) was added ethoxy propenoate derivative IV (as disclosed in U.S. Pat. No. 4,444,581, $R_1=CF_3$:70 g, 0.38M) dropwise over 1 hour so that the temperature did not exceed −10° C. The mixture was slowly warmed to room temperature, stirred for 1 hour and concentrated in vacuo. The residual oil was slowly added to a 1N HCl solution and the resulting precipitate was collected to give the desired solid thioamidopyrazole V, as a 50/50 mixture of regioisomers in 73% yield: IR (KBr): 3392, 3289, 1725 cm$^{-1}$; $^1$H NMR(CDCl$_3$): δ8.27 (s, 1H), 7.29 (broad s, 1H), 7.05 (s, 1H), 6.59 (broad s, 1H), 4.27 (m, 4H), 1.31 (m, 6H).

The following general procedure was used to synthesize the compounds listed in the Table 1:

To a −15° C. solution containing thiosemicarbazide (1 molar equivalent (meq)) in EtOH (500 mL) was added ethoxy propenoate derivative IV (1–1.1 meqs) dropwise over a 1–3 hours period so that the temperature did not exceed −10° C. The mixture was slowly warmed to room temperature, stirred for 1–3 hours and the solvent was removed in vacuo. The residual oil was slowly added to a 1N HCl solution and a precipitate was collected and dried to give a 50/50 mixture of regioisomers of the desired thioamidopyrazole V as a solid.

TABLE 1

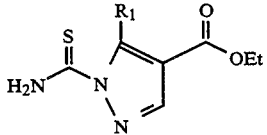

| Ex. # | $R_1$ | mp °C. |
|---|---|---|
| 1 | CF$_3$ | 96–98 |
| 2 | Ph | 158–161 |

EXAMPLE 3

2-(4-Carboethoxy-5-trifluoromethylpyrazol-1-yl)-4-(3-trifluoromethylphenyl)thiazole Bromine (15 mL, .29M) was added at room temperature to a stirred solution of 3-(trifluoromethyl)phenylacetophenone (50 g, .27M) in ether (300 mL). The mixture was stirred for 3 hours, washed with saturated NaHCO$_3$ and the organic layer was separated, dried (MgSO$_4$) and concentrated in vacuo to give 3-(trifluoromethyl)phenyacylbromide as a clear yellow oil (73 g, 99%). A mixture of the thioamide V ($R_1=CF_3$:12 g, 45 mM) and 3-(trifluoromethyl)phenylacyl bromide (11.9 g, 45 mM) in EtOH (200 mL) was stirred at reflux for 3 hours, and cooled to room temperature. The desired ester derivative VII, was isolated by filtration to give 16.1 g (82%) of solid: mp 82°–84° C.; MS:436 (MH+); $^1$H NMR (CDCl$_3$): δ8.11 (m, 3H), 7.60 (m, 3H), 4.41 (q, J=7.1 Hz, 2H), 1.40 (t, J=7.1 Hz, 3H). Elemental analyzed and calculated for (Anal. Calc'd for): Anal. Calc'd for C$_{17}$H$_{11}$F$_6$N$_3$O$_2$S: C,46.90; H,2.55; N,9.65 Found: C,46.97; H,2.57; N,9.61

The following general procedure was used to synthesize the compounds listed in the Table 2:

A mixture of an appropriately substituted thioamide V (1 meq) and a suitable phenylacyl bromide VI (1 meq) in EtOH was stirred at reflux for 1–3 hours. Upon cooling to room temperature a solid precipitated which was collected by filtration. This solid was purified (if needed) by any combination of standard techniques with include column chromatography on silica gel and recrystallization to give the desired ester derivative as a solid.

TABLE 2

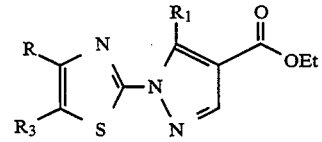

| Compound Ex. # | R | $R_1$ | mp °C. | Elemental Analysis C | H | N |
|---|---|---|---|---|---|---|
| 3 | 3-CF$_3$Ph | CF$_3$ | 82–84 | 46.97 | 2.57 | 9.61 |
| 4 | Ph | CF$_3$ | 96–98 | 52.28 | 3.17 | 11.51 |
| 5 | 3-MeOPh | CF$_3$ | 100–101 | 51.12 | 3.33 | 10.62 |
| 6 | 4-ClPh | CF$_3$ | 100–103 | 47.93 | 2.50 | 10.37 |
| 7 | 4-NO$_2$Ph | CF$_3$ | 145–148 | 46.56 | 2.65 | 13.13 |
| 8 | 4-CH$_3$Ph | CF$_3$ | 100–102 | 48.44 | 3.44 | 14.19 |
| 9 | 4-MeOPh | CF$_3$ | 84–88 | 51.27 | 3.55 | 10.67 |
| 10 | 3,4,5-(MeO)$_3$Ph | CF$_3$ | 166–168 | 49.73 | 3.92 | 9.15 |
| 11 | 3-CF$_3$Ph | CH$_3$ | 102–104 | 53.20 | 3.63 | 11.10 |
| 12 | 3-CH$_3$Ph | CF$_3$ | 89–90 | 53.52 | 3.66 | 11.23 |
| 13 | 2-CF$_3$Ph | CF$_3$ | 113–115 | 46.87 | 2.51 | 10.32 |
| 14 | 4-CF$_3$Ph | CF$_3$ | 89–91 | 46.90 | 2.42 | 9.29 |
| 15 | 3-ClPh | CF$_3$ | 102–104 | 47.67 | 2.66 | 10.32 |
| 16 | 3-CF$_3$Ph | Ph | 158–161 | 59.59 | 3.64 | 9.48 |
| 17 | 4-IPh | CF$_3$ | 85–87 | 39.15 | 2.16 | 8.58 |
| 18 | 4-ClPh | Ph | 130 | 61.36 | 3.64 | 10.21 |
| 19 | 3-CF$_3$Ph | CF$_3$ | 66–68 | 40.12 | 1.84 | 8.18 |
| 20 | 3-CF$_3$Ph | Et | 113–115 | 54.35 | 4.08 | 10.54 |
| 21 | 3-CF$_3$Ph | Pr | 123–125 | 55.34 | 4.45 | 10.37 |

*$R_3$ = H, except for Example 19 where $R_3$ = Br.

EXAMPLE 22

2-(4-Carboxy-5-trifluoromethylpyrazol-1-yl)-4-(3-trifluoromethylphenyl)thiazole

To a mixture of the pyrazole thiazole ester VII (R=3-CF$_3$Ph, $R_1$=CF$_3$: 16 g, 37 mM) in EtOH (200 mL) was added KOH (3.1 g, 55 mM). The resulting solution was stirred at reflux for 3 hours, cooled to room temperature and concentrated in vacuo. The residual semi-solid was dissolved in water, acidified with concentrated HCl and filtered to give the crude pyrazole thiazole acid X (R=3-CF$_3$Ph, $R_1$=CF$_3$) as a solid. Recrystallization of said solid from hot toluene gave the title compound as a white solid: mp 184°–186° C.; MS: 408 (MH+); $^1$H NMR (CDCl$_3$): δ8.10 (m, 2H), 7.64 (m,2H), 7.26 (2s, 2H). Anal. Calc'd for $C_{15}H_7F_6N_3O_2S$: C, 44.23; H,1.73; N,10.32 Found: C, 44.13; H,1.41; N,10.21

The following general procedure was used to synthesize the compounds listed in the Table 3:

To a mixture of an appropriate pyrazole thiazole ester VII (1 meq) in EtOH was added KOH (2–4 meqs). The resulting solution was stirred at reflux for 1–3 hours, cooled to room temperature and concentrated in vacuo. The residual semi-solid was dissolved in water, acidified with concentrated HCl and filtered to give a solid. This solid was purified by recrystallization from a suitable organic solvent to give the desired acid derivative X. If a solid did not form after being acidified then the mixture was extracted with successive portions of ether and ethyl acetate. The organic extracts were dried (MgSO4), concentrated in vacuo and recrystallized from toluene to give the desired acid derivative X as a solid.

TABLE 3

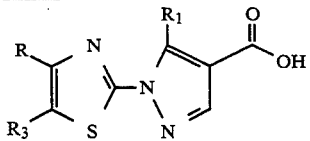

| Compound Ex # | R | $R_1$ | mp °C | Elemental Analysis C | H | N |
|---|---|---|---|---|---|---|
| 22 | 3-CF3Ph | CF3 | 184–86 | 44.13 | 1.41 | 10.21 |
| 23 | Ph | CF3 | 178–80 | 50.17 | 2.30 | 12.07 |
| 24 | 3-MeOPh | CF3 | 168–70 | 48.44 | 3.44 | 14.19 |
| 25 | 4-ClPh | CF3 | 202–04 | 44.94 | 1.55 | 11.02 |
| 26 | 4-NO2Ph | CF3 | 225–27 | 43.92 | 1.66 | 14.34 |
| 27 | 3-CF3Ph | CF3 | 166–169 | 37.02 | 1.29 | 8.48 |
| 28 | 3-CF3Ph | CH3 | 223–25 | 51.07 | 2.78 | 11.73 |
| 29 | 3-CH3Ph | CF3 | 176–78 | 50.99 | 2.60 | 11.92 |
| 30 | 4-CF3Ph | CF3 | 190–92 | 44.04 | 4.27 | 9.98 |
| 31 | 2-CF3Ph | CF3 | 170–73 | 44.49 | 1.80 | 10.01 |
| 32 | 3-ClPh | CF3 | 199–201 | 44.67 | 1.65 | 10.96 |
| 33 | 3-CF3Ph | Ph | 189–90 | 57.61 | 2.81 | 10.08 |

$R_3$ = H, except for Example 27 where $R_3$ = Br.

EXAMPLE 34

2-[4-[2-N,N-Diethylamino)ethylcarbamoyl]-5-(trifluoromethyl)pyrazol-1-yl]-4-(3-trifluoromethylphenyl) thiazole A mixture of 22:1.5 g, 3.7 mM) and carbonyldiimidazole (0.66 g, 4.1 mM) in DMF (30 mL) was stirred at room temperature for 1 hour. 1,1-Diethylethylenediamine (2.5 mL, 17.5 mM) was added to the mixture and the reaction was stirred overnight. The resulting mixture was poured into water and a precipitate was collected. The crude solid XI (A=-C(O)NH, B=(CH2)2, NR4R5=NEt2, R=3-CF3Ph, R1=CF3, R3=H) was purified by column chromatography on silica gel using methanol/methylene chloride (1:9) as an eluent. The desired fractions were concentrated in vacuo and recrystallized from methylene chloride/hexane to give the title compound as a white solid: mp 111°–113° C.; MS: 506 (MH+). Anal. Calc'd for $C_{21}H_{21}F_6N_5OS$: C,49.89; H,4.19; N,13.86 Found: C,49.46; H,3.93; N,13.75

The following general procedure was used in the preparation of the compounds listed in Table 4:

A mixture of 2-carboxypyrazole thiazole X (1 meq) and carbonyldiimidazole (1.1 meq) in DMF was stirred at room temperature for 1–4 hours. An appropriately substituted diamine (3–6 meqs) was added to the mixture and the reaction was stirred overnight. The resulting mixture was poured into water and a precipitate was collected. If a precipitate does not form, then the mixture was extracted into an organic solvent such as ethyl acetate or methylene chloride. The organic extracts were dried (MgSO4) and concentrated in vacuo. The crude product was then purified by any of the standard methods which include column chromatography and recrystallization to give the title compound as a solid. Likewise, treatment of the solid with an acid such as conc. hydrochloric acid, conc. hydrobromic acid, oxalic acid, lactic acid, citric acid or succinic acid in a solvent such as methanol, acetone or diethyl ether provided the corresponding salt.

TABLE 4

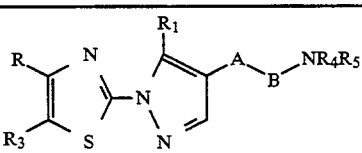

| Compound Ex. # | R | $R_1$ | A—B—N $R_4R_5$ | mp °C | Elemental Analysis C | H | N |
|---|---|---|---|---|---|---|---|
| 34 | 3-CF3Ph | CF3 | C(O)NH(CH2)2NEt2 | 111–113 | 49.46 | 3.93 | 13.75 |
| 35 | 4-NO2Ph | CF3 | C(O)NH(CH2)2NEt2 | 183–184 | 49.84 | 4.34 | 17.50 |
| 36 | 4-NO2Ph | CF3 | C(O)NH(CH2)3NMe2 | 191–193 | 48.75 | 3.81 | 17.90 |
| 37 | 3-CF3Ph | CF3 | C(O)NH(CH2)3NEt2 | 118–120 | 47.19 | 4.10 | 12.41 |
| 38 | 3-CF3Ph | CF3 | C(O)NH(CH2)3NBu2 | 95–97 | 54.56 | 5.64 | 12.24 |
| 39 | 3-CF3Ph | CF3 | C(O)NH(CH2)3NMe2 | 146–147 | 48.44 | 3.44 | 14.19 |
| 40 | 3-CH3OPh | CF3 | C(O)NH(CH2)3NEt2 | 108–110 | 54.73 | 5.20 | 14.89 |
| 41 | 4-CH3OPh | CF3 | C(O)NH(CH2)3NEt2 | 87–89 | 54.35 | 5.27 | 4.28 |
| 42 | 4-CH3OPh | CF3 | C(O)NH(CH2)3NBu2 | 93–95 | 58.05 | 6.04 | 12.93 |
| 43 | 4-CH3Ph | CF3 | C(O)NH(CH2)3NEt2 | 86–88 | 56.32 | 5.39 | 14.72 |
| 44 | 4-ClPh | CF3 | C(O)NH(CH2)3NEt2 | 98–100 | 51.85 | 4.95 | 14.39 |
| 45 | 4-CH3Ph | CF3 | C(O)NH(CH2)3NBu2 | 76–78 | 59.63 | 6.52 | 13.45 |
| 46 | 3-CF3Ph | CF3 | C(O)NH(CH2)3NEt2 | 129–131 | 57.29 | 5.63 | 12.82 |
| 47 | 3,4,5-(MeO)3Ph | CF3 | C(O)NH(CH2)3NEt2 | 99–101 | 44.10 | 3.54 | 11.61 |
| 48 | 3-CF3Ph | CH3 | C(O)NH(CH2)3NEt2 | 104–106 | 56.45 | 5.74 | 15.06 |
| 49 | 3-CF3Ph | CH3 | C(O)C(O)NH(CH2)3NBu2 | 99–100 | 60.11 | 6.66 | 13.67 |
| 50 | Ph | CF3 | C(O)NH(CH2)3NEt2 | 88–90 | 55.31 | 5.34 | 15.04 |
| 51 | 3-CF3Ph | CF3 | C(O)NH(CH2)2pyrrolidine | 173–74 | 49.86 | 3.71 | 13.52 |

TABLE 4-continued

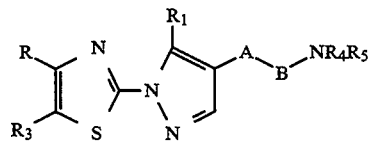

| Compound Ex. # | R | $R_1$ | A—B—N $R_4R_5$ | mp °C. | C | H | N |
|---|---|---|---|---|---|---|---|
| 52 | 3-CF$_3$Ph | CF$_3$ | C(O)NH(CH$_2$)$_4$NEt$_2$ | 98–101 | 51.12 | 4,67 | 12.58 |
| 53 | 3-CF$_3$Ph | CF$_3$ | C(O)NH(CH$_2$)$_3$pyrrolidinone | 156–158 | 49.31 | 3.87 | 13.43 |
| 54 | 3-CF$_3$Ph | CF$_3$ | C(O)NH(CH$_2$)$_3$-2-pipecoline | 122–25 | 52.84 | 4.64 | 12.75 |
| 55 | 3-CH$_3$Ph | CF$_3$ | C(O)NH(CH$_2$)$_2$piperidine | 167–169 | 56.99 | 4.98 | 15.00 |
| 56 | 4-CF$_3$Ph | CF$_3$ | C(O)NH(CH$_2$)$_3$NEt$_2$ | 105–106 | 50.68 | 4.27 | 13.60 |
| 57 | 4-CF$_3$Ph | CF$_3$ | C(O)NH(CH$_2$)$_2$piperidine | 140–143 | 51.16 | 3.91 | 13.76 |
| 58 | 3-ClPh | CF$_3$ | C(O)NH(CH$_2$)$_3$NEt$_2$ | 92–95 | 51.61 | 4.76 | 14.62 |
| 59 | 3-CF$_3$Ph | CF$_3$ | C(O)NH(CH$_2$)$_7$NEt$_2$ | 104–05 | 53.89 | 5.47 | 12.03 |
| 60 | 3-CF$_3$Ph | Ph | C(O)NH(CH$_2$)$_3$NEt$_2$ | 121–123 | 61.48 | 5.45 | 13.11 |
| 61 | 3-CF$_3$Ph | CF$_3$ | C(O)NH(CH$_2$)$_5$NH$_2$ | 223–25 | 44.58 | 3.51 | 12.76 |
| 62 | 3-CF$_3$Ph | CF$_3$ | C(O)NH(CH$_2$)$_4$NH$_2$ | 225–28 | 44.49 | 3.55 | 13.25 |
| 63 | 3-CF$_3$Ph | CF$_3$ | C(O)NMe(CH$_2$)$_3$piperidine | 140–141 | 52.73 | 4.51 | 12.73 |
| 64 | 3-CF$_3$Ph | CF$_3$ | C(O)NH(CH$_2$)$_2$NMe$_2$ | 145–146 | 44.22 | 3.15 | 12.13 |
| 65 | 3-CF$_3$Ph | H | C(O)NH(CH$_2$)$_3$NEt$_2$ | 102–103 | 50.66 | 4.82 | 12.76 |
| 66 | 3-CF$_3$Ph | CF$_3$ | C(O)NH(CH$_2$)$_2$NH$_2$ | 264–66 | 41.84 | 2.45 | 14.24 |
| 67 | 3-BrPh | CF$_3$ | C(O)NH(CH$_2$)$_3$NH$_2$ | 254–256 | 40.11 | 2.97 | 13.58 |
| 68 | 4-MeOPh | CF$_3$ | C(O)NH(CH$_2$)$_3$imidazole | 171–173 | 45.81 | 3.92 | 14.46 |
| 69 | 3-CF$_3$Ph | Ph | C(O)NH(CH$_2$)$_3$pyrrolidine | 105–110 | 58.24 | 4.70 | 12.96 |
| 70 | 3-CF$_3$Ph | Ph | C(O)NH(CH$_2$)$_3$imidazole | 162 | 59.50 | 4.19 | 15.90 |
| 71 | 3-ClPh | Ph | C(O)NH(CH$_2$)$_3$imidazole | 143–155 | 58.86 | 4.37 | 16.53 |
| 72 | 3-CF$_3$Ph | CF$_3$ | C(O)NH(CH$_2$)$_4$NMe$_2$ | 113–116 | 53.31 | 5.35 | 12.35 |
| 73 | 3-HOPh | CF$_3$ | C(O)NH(CH$_2$)$_2$piperidine | 137–140 | 54.18 | 5.61 | 14.00 |
| 74 | 4-ClPh | C$_3$H$_7$ | C(O)NH(CH$_2$)$_3$pyrrolidine | 136–138 | 58.57 | 5.29 | 14.72 |
| 75 | 4-ClPh | C$_2$H$_5$ | C(O)NH(CH$_2$)$_3$pyrrolidine | 110–112 | 57.70 | 5.11 | 15.25 |
| 76 | 4-ClPh | C$_3$H$_7$ | C(O)NH(CH$_2$)$_3$imidazole | 162–164 | 57.45 | 4.83 | 18.32 |
| 77 | 3-CF$_3$Ph | CH$_3$ | C(O)NHCH$_2$C(CH$_3$)$_2$CH$_2$NH$_2$ | 184–187 | 54.38 | 4.94 | 15.73 |
| 78 | 3-CF$_3$ | CF$_3$ | C(O)NH(CH$_2$)$_3$NEt$_2$ | 143–145 | 40.54 | 3.93 | 13.07 |

$R_3$ = H, except for example 46 where $R_3$ = Br.

EXAMPLE 79

2-[4-(3-Bromopropylcarbamoyl)-5-(trifluoromethyl)-pyrazol-1-yl]-4-(3-trifluoromethylphenyl)thiazole A mixture of 22:4.7 g, 11.6 mM) and carbonyldiimidazole (2.8 g, 17.3 mM) in DMF (30 mL) was stirred at room temperature for 30 min. 3-Bromopropylamine hydrobromide (12.7 g, 58 mM) was added and the resulting amber solution was stirred at room temperature for 2 hours, poured into water (100 mL) and stirred overnight at room temperature. The resulting precipitate was collected by filtration and dried to give the title compound as a white solid: mp 187°–190° C.; MS: 528 (MH+); $^1$H NMR (DMSO-d$_6$): δ8.82 (m, 1H), 8.45 (s, 1H), 8.30 (m, 3H), 7.77 (m, 2H), 3.61 (t, J=2.2 Hz, 2H), 3.38 (m, 2H), 2.06 (p, J=2.2 Hz, 2H). Anal. Calc'd for C$_{18}$H$_{13}$BrF$_6$N$_4$OS: C,41.00; H,2.48; N,10.63 Found: C,41.26; H,2.46; N,10.24

The following general procedure was used in the synthesis of the compounds contained in Table 5:

A mixture of an appropriate carboxypyrazole thiazole X (1 meq) and carbonyldiimidazole (1.5–2.0 meqs) in DMF was stirred at room temperature for 0.5–2 hours. 3-Bromopropylamine hydrobromide (2.5–6 meqs) was added and the resulting solution was stirred at room temperature for 1–2 hours, poured into water and stirred at room temperature. The resulting precipitate was collected by filtration and dried to give the desired bromide XII (A=C-(O)NH, B=(CH$_2$)$_3$, halogen=Br) as a solid.

TABLE 5

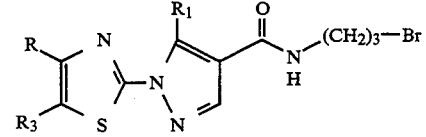

| Compound Ex. # | R | $R_1$ | mp °C. | C | H | N |
|---|---|---|---|---|---|---|
| 79 | 3-CF$_3$Ph | CF$_3$ | 187–90 | 41.26 | 2.46 | 10.24 |
| 80 | 3-CF$_3$Ph | CH$_3$ | 99–100 | 60.11 | 6.66 | 13.67 |
| 81 | Ph | CF$_3$ | 155–57 | 44.90 | 3.04 | 11.71 |
| 82 | 4-CH$_3$Ph | CF$_3$ | 177–79 | 45.69 | 3.30 | 11.53 |
| 83 | 3-CH$_3$Ph | CF$_3$ | 147–50 | 45.38 | 3.53 | 11.64 |
| 84 | 2-CF$_3$Ph | CF$_3$ | 113–15 | 41.03 | 2.49 | 10.50 |
| 85 | 4-CF$_3$Ph | CF$_3$ | 178–81 | 41.06 | 2.35 | 10.67 |
| 86 | 3-ClPh | CF$_3$ | 182–83 | 41.46 | 2.52 | 11.32 |
| 87 | 3-CF$_3$Ph | Ph | 167–68 | 51.60 | 3.39 | 10.46 |
| 88 | 3-ClPh | Pr | 175–177 | 48.65 | 4.29 | 12.07 |

$R_3$ = H.

EXAMPLE 89

2-[4-[3-(N-Piperidino)propylcarbamoyl]-5-(trifluoromethyl)pyrazol-1-yl]-4-(3-trifluoromethylphenyl)thiazole A mixture of the bromide XII (A=C(O)NH, B=(CH$_2$)$_3$, halogen=Br, R=3-CF$_3$Ph, R$_1$=CF$_3$: 1.4 g, 2.6 mM) and piperidine (2.6 mL, 26 mM) in DMF (5 mL) was stirred at room temperature for 2 hours and poured into water. The aqueous mixture was stirred at room temperature overnight and the resulting white solid collected to give 1.1 g (84%) of the title compound: mp 126°–128° C.; MS: 532 (MH+). Anal. Calc'd for $C_{23}H_{23}F_6N_5OS$: C, 51.97; H,4.36; N,13.18 Found: C, 51.83; H,4.09; N,13.30

The following general procedure was used in the preparation of the compounds listed in Table 6:

A mixture of the an appropriately substituted carbamoyl bromide XII (1 meq) and an amine (1–10 meqs) in DMF (5 mL) was stirred at room temperature for 1–24 hours. The resulting mixture was poured into water and stirred until a precipitate formed. The resulting mixture was poured into water and a precipitate was collected. If a precipitate does not form, then extracted into an organic solvent such as ethyl acetate or methylene chloride. The organic extracts were dried ($MgSO_4$) and concentrated in vacuo. The crude product was then purified by any of the standard methods which include column chromatography and recrystallization to give the title compound as a solid. Likewise, treatment of the solid with an acid such as conc. hydrochloric acid, conc. hydrobromic acid, oxalic acid, lactic acid, citric acid or succinic acid in a solvent such as methanol, acetone or diethyl ether provided the corresponding salt.

EXAMPLE 121

2-[4-(3-Aminopropylcarbamoyl)-5-(trifluoromethyl)-pyrazol-1-yl]-4-(3-trifluoromethylphenyl)thiazole Monohydrochloride A mixture of bromide XII (A=C(O)NH, B=$(CH_2)_3$, halogen=Br, R=3—$CF_3$Ph, $R_1$=$CF_3$: 5.0 g, 9.5 mM) and sodium azide (3.0 g, 46.0 mM) in DMF (10 mL) was slowly warmed up to 90° C. and stirred for 2 hours. The resulting mixture was cooled to room temperature, poured into water and stirred at room temperature overnight. The resulting white solid was collected and dried to give 4.6 g (100%) of the azide derivative XIII (A=C(O)NH, B=$(CH_2)_3$, R=3—$CF_3$Ph, $R_1$=$CF_3$) as a solid: mp 158°–160° C.; MS: 490 (MH+); $^1H$ NMR($CDCl_3$): δ8.10 (m, 2H), 7.92 (s, 1H), 7.60 (m, 3H), 6.19 (br s, 1H), 3.55 (q, J=2.2 Hz, J=2.0 Hz, 2H), 3.47 (t, J=2.1 Hz, 2H), 1.92 (m, 1H). A mixture of the azide XIII (A=—C(O)NH, B=$(CH_2)_3$, R=3—$CF_3$Ph, $R_1$=$CF_3$: 1.0 g, 2.0 mM) and triphenylphosphine (1.18 g, 4.5 mM) in DMF (10 mL) was stirred at room temperature overnight. The reaction mixture was concentrated in vacuo leaving a residue which was dissolved in acetone, and purified by column chromatography on silica gel using acetone/methanol/triethylamine (7:2:1) as an eluent. Crystallization of the desired fractions from ethyl acetate/ether to give 0.9 g (95%) of the free base of the title compound as a white crystalline solid.

TABLE 6

| Compound Ex. # | R | $R_1$ | A—B—N $R_4R_5$ | C | H | N | mp °C. |
|---|---|---|---|---|---|---|---|
| 89 | 3-$CF_3$Ph | $CF_3$ | C(O)NH$(CH_2)_3$piperidine | 51.83 | 4.09 | 13.30 | 126–128 |
| 90 | 3-$CF_3$Ph | $CF_3$ | C(O)NH$(CH_2)_3$pyrrolidine | 51.06 | 4.14 | 13.35 | 148–150 |
| 91 | 3-$CF_3$Ph | $CH_3$ | C(O)NH$(CH_2)_3$piperidine | 57.66 | 5.34 | 14.44 | 128–130 |
| 92 | 4-$CH_3$Ph | $CF_3$ | C(O)NH$(CH_2)_3$piperidine | 57.56 | 5.35 | 14.38 | 139–141 |
| 93 | 4-$CH_3$Ph | $CF_3$ | C(O)NH$(CH_2)_3$pyrrolidine | 56.93 | 5.25 | 14.88 | 146–148 |
| 94 | Ph | $CF_3$ | C(O)NH$(CH_2)_3$piperidine | 56.44 | 5.15 | 14.75 | 140–142 |
| 95 | 3-$CF_3$Ph | $CF_3$ | C(O)NH$(CH_2)_3$pyrrolidine | 55.62 | 4.87 | 15.15 | 141–143 |
| 96 | 4-$CH_3$Ph | $CF_3$ | C(O)NH$(CH_2)_3$cyclohexylamine | 57.26 | 6.03 | 13.91 | 141–142 |
| 97 | 3,4-$Cl_2$Ph | $CF_3$ | C(O)NH$(CH_2)_3$piperidine | 44.75 | 4.11 | 11.52 | 210–13 |
| 98 | 3-$CH_3$Ph | $CF_3$ | C(O)NH$(CH_2)_3$piperidine | 57.00 | 5.30 | 14.33 | 153–155 |
| 99 | 3-$CH_3$Ph | $CF_3$ | C(O)NH$(CH_2)_3$pyrrolidine | 56.56 | 4.97 | 14.78 | 155–158 |
| 100 | 2-$CF_3$Ph | $CF_3$ | C(O)NH$(CH_2)_3$piperidine | 51.89 | 4.37 | 13.43 | 135–138 |
| 101 | 2-$CF_3$Ph | $CF_3$ | C(O)NH$(CH_2)_3$pyrrolidine | 50.96 | 4.06 | 13.51 | 86–88 |
| 102 | 3-$CF_3$Ph | $CF_3$ | C(O)NH$(CH_2)_3$cyclohexylamine | 52.60 | 4.62 | 12.78 | 128–130 |
| 103 | 3-$CF_3$Ph | $CF_3$ | C(O)NH$(CH_2)_3$cyclopentylamine | 51.43 | 4.42 | 12.89 | 137–138 |
| 104 | 4-$CF_3$Ph | $CF_3$ | C(O)NH$(CH_2)_3$pyrrolidine | 51.06 | 4.20 | 13.40 | 159–161 |
| 105 | 4-$CF_3$Ph | $CF_3$ | C(O)NH$(CH_2)_3$cyclohexylamine | 52.38 | 4.63 | 13.22 | 135–137 |
| 106 | 3-ClPh | $CF_3$ | C(O)NH$(CH_2)_3$piperidine | 52.92 | 4.54 | 13.89 | 144–146 |
| 107 | 3-ClPh | $CF_3$ | C(O)NH$(CH_2)_3$cyclohexylamine | 52.65 | 4.83 | 13.15 | 150–152 |
| 108 | 3-$CF_3$Ph | Ph | C(O)NH$(CH_2)_3$cyclohexylmaine | 62.72 | 5.48 | 12.51 | 150–152 |
| 109 | 3-$CF_3$Ph | $CF_3$ | C(O)NH$(CH_2)_3$hexa-methyleneimine | 52.86 | 4.57 | 12.82 | 93–95 |
| 110 | 3-$CF_3$Ph | $CF_3$ | NH$(CH_2)_3$methyl piperazine | 50.75 | 4.22 | 15.00 | 142–143 |
| 111 | 3-$CF_3$Ph | $CF_3$ | C(O)NH$(CH_2)_3$hepta-methyleneamine | 53.57 | 4.73 | 12.52 | 99–102 |
| 112 | 3-$CF_3$Ph | $CF_3$ | C(O)C(O)NH$_2$$(CH_2)_3$NHisopropyl | 49.92 | 4.17 | 13.80 | 154–155 |
| 113 | 3-$CF_3$Ph | $CF_3$ | C(O)NH$(CH_2)_3$NHbutyl | 50.90 | 4.43 | 13.49 | 129–130 |
| 114 | 3-$CF_3$Ph | $CF_3$ | C(O)NH$(CH_2)_3$NHpropyl | 49.86 | 4.20 | 13.50 | 136–138 |
| 115 | Ph | $CF_3$ | C(O)NH$(CH_2)_3$piperdine | 51.17 | 5.25 | 11.79 | 140–142 |
| 116 | 3-$CF_3$Ph | $CF_3$ | C(O)NH$(CH_2)_3$methyl piperazine | 45.87 | 4.24 | 13.95 | 142–143 |
| 117 | 3-$CF_3$Ph | $CF_3$ | C(O)NH$(CH_2)_3$cyclohexylamine | 50.93 | 4.13 | 12.67 | 209–212 |
| 118 | Ph | $CF_3$ | C(O)NH$(CH_2)_3$cyclohexylamine | 50.43 | 5.23 | 12.15 | 146–148 |
| 119 | 4-MeOPh | $CF_3$ | C(O)NH$(CH_2)_3$methyl piperazine | 45.87 | 4.24 | 13.95 | 158–160 |
| 120 | 3-$CF_3$Ph | Ph | C(O)NH$(CH_2)_3$methyl piperazine | 60.05 | 5.26 | 14.71 | 144–147 |

*$R_3$ = H, except Example 116 and 119 where $R_3$ = Br.

Concentrated HCl was added to a mixture of the free base in methanol followed by trituration with ether to give the title compound as a white solid: mp 263°–266° C. (decomposed); MS: 464 (MH+); $^1$H NMR (DMSO-d6): δ8.92 (m, 1H), 8.46 (s, 1H), 8.28 (m, 3H), 7.96 (broad s, 2H), 7.76 (m, 2H), 3.50 (m, 2H), 2.86 (t, J=2.5 Hz, 2H), 1.82 (m, 2H). Anal. Calc'd for $C_{18}H_{15}F_6N_5OS·HCl$: C, 43.25; H, 3.23; N, 14.01 Found: C, 43.31; H, 3.29; N, 13.70

The following general procedure was used to synthesize the compounds listed in Table 7:

A mixture of an appropriately substituted bromide XII and a 4–6 Molar excess of sodium azide in DMF was slowly warmed up to 80°–100° C. and stirred for 2–4 hours. The resulting mixture was cooled to room temperature, poured into water and stirred at room temperature overnight. The resulting white solid was collected and dried to give 4.6 g (100%) of the desired azide derivative XIII (A=C(O)NH, B=(CH$_2$)$_3$) as a solid.

A mixture of the appropriate azide derivative XIII (A=—C(O)NH, B=CH$_2$, n=3: 1 meq) and triphenylphosphine (1–1.1 meqs) in DMF was stirred at room temperature overnight. The reaction mixture was concentrated in vacuo leaving a residue which was purified by column chromatography on silica gel. Crystallization of the desired fractions from the free base of the amino derivative X IV (A=C(O)NH, B=(CH$_2$)$_3$, NR$_4$R$_5$=NH$_2$), as a white crystalline solid.

TABLE 7

| Compound Ex. # | R | R$_1$ | Elemental Analysis C | H | N | mp °C. |
|---|---|---|---|---|---|---|
| 121 | 3-CF$_3$Ph | CF$_3$ | 43.31 | 3.29 | 13.70 | 263–66 |
| 122 | 3-ClPh | CF$_3$ | 43.71 | 3.48 | 14.75 | 240–42 |
| 123 | 4-CH$_3$Ph | CF$_3$ | 48.50 | 4.35 | 15.83 | 152–54 |
| 124 | 3-CF$_3$Ph | CF$_3$ | 40.11 | 2.97 | 13.58 | 254–56 |
| 125 | 4-CF$_3$Ph | CF$_3$ | 37.19 | 2.64 | 11.93 | 246–49 |
| 126 | 3-ClPh | Ph | 56.07 | 4.37 | 14.78 | 205–07 |
| 127 | 3-ClPh | C$_3$H$_7$ | 55.74 | 5.53 | 17.20 | 145–47 |

R$_3$ = H except for Example 124 where R$_3$ = Br.

EXAMPLE 128

2-[4-(3-Guanidinopropylcarbamoyl)-5-(trifluoromethyl)-pyrazol-1-yl]-4-(3-trifluoromethylphenyl)thiazole Nitrate A mixture of the amino derivative XIV (A=C(O)NH, B=(CH$_2$)$_3$, NR$_4$R$_5$=NH$_2$, R=3—CF$_3$Ph, R$_1$=CF$_3$: 1.35 g, 2.9 mM), triethylamine (1.2 mL, 8.7 mM) and 1-guanyl-3,5-dimethylpyrazole nitrate (Can. J. Chem. 36, 1541, 1958) (1.17 g, 5.8 mM) in DMF (30 mL) was stirred at 50°–60° C. for 4 hours and cooled to room temperature. The DMF was removed under reduced pressure and the oily residue was triturated with ether to give a residue. This semi-solid residue was diluted with water, stirred at room temperature for 3 hours, and recrystallized from MeOH/Et$_2$O to give the title compound as a white solid: mp 198°–201° C.; MS: 506 (MH+); $^1$H NMR(DMSO-d$_6$): δ8.78 (t, J=1.8 Hz, 1H), 8.45 (s, 1H), 8.29 (m, 3H), 7.77 (m, 2H), 7.49 (t, 1.8 Hz, 1H), 7.15 (brs, 4H), 3.36 (sharp singlet), 3.29 (q, J=2.2 Hz, J=2.0 Hz, 2H), 3.19 (q, J=2.2 Hz, J=2.0 Hz, 2H), 1.73 (m, 2H). Anal. Calc'd for $C_{19}H_{17}F_6N_7OS·HNO_3$: C, 40.15; H, 3.19; N, 19.71 Found: C, 40.38; H, 3.15; N, 19.45

The following general procedure was used in the synthesis of the compounds listed in Table 8:

A mixture of an appropriately substituted amino derivative XIV (A=C(O)NH, B=(CH$_2$)$_3$, NR$_4$R$_5$=NH$_2$: 1 meq), triethylamine (2–3 meqs) and 1-quanyl-3,5-dimethylpyrazole nitrate (2 meqs) in DMF was stirred at 50°–80° C. for 3–4 hours and cooled to room temperature. The DMF was removed under reduced pressure and the oily residue was triturated with ether to give a residue. This semi-solid residue was diluted with water, stirred at room temperature for 3–16 hours, and recrystallized to give the desired guanidine derivative XVI (A=C(O)NH, B=(CH$_2$)$_3$), as a white solid.

TABLE 8

| Compound Ex. # | R | R$_1$ | Elemental Analysis C | H | N | mp °C. |
|---|---|---|---|---|---|---|
| 128 | 4-CF$_3$Ph | CF$_3$ | 44.41 | 3.95 | 21.58 | 156–60 |
| 129 | 3-ClPh | CF$_3$ | 40.57 | 3.34 | 20.80 | 184–86 |
| 130 | 4-CF$_3$Ph | CF$_3$ | 44.41 | 3.95 | 21.58 | 156–60 |

R$_3$ = H.

EXAMPLE 131

2-[4-[3-(N,N-Dimethylforamidinyl)propylcarbamoyl]-5-(trifluoromethyl)pyrazol-1-yl]-4-(3-trifluoromethylphenyl)thiazole A mixture of amino derivative XIV (A=C(O)NH, B=(CH$_2$)$_3$, NR$_4$R$_5$=NH$_2$, R=3—CF$_3$Ph, R$_1$=CF$_3$: 1.0 g, 2.1 mM) and DMF-dimethylacetal (0.6 mL) in MeOH (20 mL) was stirred at reflux for 6 hours and concentrated in vacuo. The resulting residue was purified by column chromatography using triethylamine/acetone (2:8) as an eluent and crystallized from methanol/ether to give the title compound as a solid: mp 160°–163° C., MS: 519 (MH+). Anal. Calc'd for $C_{21}H_{20}F_6N_6OS$: C, 48.65; H, 3.89; N, 16.21 Found: C, 48.30; H, 3.82; N, 15.94

EXAMPLE 132

2-[4-(3-(N,N-Dimethylformamidinyl)propylcarbamoyl]5-(trifluoromethyl)pyrazol-1-yl]-4-(3-chlorophenyl)thiazole A mixture of amino derivative XIV (A=C(O)NH, B=(CH$_2$)$_3$, NR$_4$R$_5$=NH$_2$, R=3-ClPh, R$_1$=CF$_3$: 3.0 g, 7.0 mM) and DMF-dimethylacetal (1.9 mL, 14 mM) in MeOH (20 mL) was stirred at reflux for 6 hours and concentrated in vacuo. The resulting residue was purified by column chromatography using triethylamine/acetone (2:8) as an eluent and crystallized from methanol/ether to give the title compound as a solid: mp 158°–161° C.; MS: 485 (MH+). Anal. Calc'd for $C_{20}H_{20}ClF_3N_6OS$: C, 49.54; H, 4.16; N, 17.33 Found: C, 49.38; H, 4.02; N, 16.97

EXAMPLE 133

2-[4-Hydroxymethyl]-5-(trifluoromethyl)pyrazol-1-yl]-4-(3-trifluoromethylphenyl)thiazole

A 1.0M solution of borane tetrahydrofuran complex (35 mL, 35 mM) was added to a stirred solution of ester VII (R=3—CF$_3$Ph, R$_1$=CF$_3$: 4.65 g, 10.7 mM) in THF (40 mL) at 0° C. The mixture was heated to reflux for 6 hours, and cooled to 0° C. Water (20 mL) was added to the resulting mixture, followed by the addition of 1N NaOH (20 mL) and gentle warming to room temperature. The organic layer was separated and the aqueous layer was washed with ethyl acetate. The organic extracts were combined, dried (MgSO$_4$) filtered and concentrated in vacuo to give an oily residue. The residue was purified by column chromatography on silica gel using methylene chloride as an eluent to give the title compound (2.68 g, 64%) as a solid: mp 97°-99° C.; MS: 394 (MH+). Anal. Calc'd for C$_{15}$H$_9$F$_6$N$_3$OS: C, 45.81; H, 2.31; N, 10.68 Found: C, 46.04; H, 2.34; N, 10.81

EXAMPLE 134

2-[4-[3-(N-Piperidino)propyl)aminomethyl]-5-(trifluoromethyl)pyrazol-1-yl]-4-(3-trifluoromethylphenyl)thiazole

A mixture of alcohol XX (R=3—CF$_3$Ph, R$_1$=CF$_3$: 0.54 g, 1.4 mM) and pyridinium chlorochromate (0.55 g, 2.7 mM) in methylene chloride was stirred at room temperature for 3 hours. The resulting mixture was filtered through a pad of celite, concentrated in vacuo, diluted with ether and filtered again through a pad of celite. The mother liquor was concentrated in vacuo to give the desired aldehyde XXI (R=3—CF$_3$Ph, R$_1$=CF$_3$: 0.6 g) as a white solid; MS: 392 (MH+). To a suspension of 1-bromopropylamine hydrobromide (1.7 g, 7.6 mM) and molecular sieves in MeOH, was added aldehyde XXI (0.5 g, 1.3 mM) followed by sodium cyanoborohydride (44.0 mg, 0.7 mM). The resulting mixture was stirred overnight at room temperature. The reaction was acidified with conc. HCl (pH<2), filtered through celite, and concentrated in vacuo. The residue was diluted with water and extracted with ether. The aqueous layer was adjusted to pH 10 with solid KOH and extracted several times with ether. The combined organic extracts were dried (MgSO$_4$), filtered and concentrated in vacuo. The residue was purified by column chromatography on silica gel using methylene chloride as an eluent to give the intermediate bromide; MS: 514 (MH+). A mixture of the bromide (0.6 g, 1.2 mM) and piperidine was stirred at room temperature for 3 hours, concentrated in vacuo and purified by column chromatography to give an oil. This oil was dissolved in acetone and converted to its oxalate salt. The title compound precipitated out of this mixture as a white crystalline solid: mp 197°-198° C. MS: 518 (MH+). Anal. Calc'd for C$_{23}$H$_{25}$F$_6$N$_5$S·(C$_2$H$_2$O$_4$)$_2$: C, 46.49; H, 4.19; N, 10.04 Found: C, 46.76; H, 4.44; N, 10.42

EXAMPLE 135

2-[4-[(N-Cyclohexylamino)butoxymethyl]-5-(trifluoromethyl)-pyrazol-1-yl]-4-(3-trifluoromethylphenyl)thiazole Hemisuccinate

A stirred mixture of 1-bromo-4-chlorobutane (0.6 mL, 5.95 mM), KOH (0.37 g, 6.6 mM) and alcohol XX (R=3—CF$_3$Ph, R$_1$=CF$_3$: 1.3 g, 3.3 mM) in acetone (50 mL) was stirred at reflux for 24 hours. The resulting mixture was concentrated in vacuo and diluted with ethyl acetate and water. The organic layer was dried (MgSO$_4$), concentrated in vacuo and purified by column chromatography to give 2-[4-[4-chlorobutoxymethyl]-5-(trifluoromethyl)-pyrazol-1-yl]-4-(3-trifluoromethylphenyl)thiazole as an amber oil: MS: 484 (MH+). The above chlorobutoxy derivative (0.66 g, 1.4 mM) and cyclohexylamine (2 mL, 17.4 mM) in DMF (5 mL) was stirred at 110° C. for 5 hours. The resulting mixture was concentrated in vacuo, diluted with acetone and purified by column chromatography using EtOAc/MeOH as an eluent to give the title compound as an oil which was converted to its succinate salt; mp 150°-152° C. MS: 547 (MH+). Anal. Calc'd for C$_{25}$H$_{28}$F$_6$N$_4$OS.½C$_4$H$_6$O$_4$: C, 53.55; H, 5.16; N, 9.25 Found: C, 53.48; H, 4.93; N, 9.10

EXAMPLE 136

2-[4-[3-(N-Piperidino)propoxymethyl]-5-(trifluoromethyl)pyrazol-1-yl]-4-(3-trifluoromethylphenyl)thiazole Oxalate

A stirred mixture of 1-bromo-3-chloropropane (0.6 mL, 5.95 mM), KOH (0.37 g, 6.6 mM) and alcohol XX (R=3—CF$_3$Ph, R$_1$=CF$_3$: 1.3 g, 3.3 mM) in acetone (50 mL) was stirred at reflux for 24 hours. The resulting mixture was concentrated in vacuo and diluted with ethyl acetate and water. The organic layer was dried (MgSO$_4$), concentrated in vacuo and purified by column chromatography to give 2-[4-[3-chloropropoxymethyl]-5-(trifluoromethyl)-pyrazol-1-yl]-4-(3-trifluoromethylphenyl)thiazole as an amber oil (0.56 g, 37%); MS: 470 (MH+).

The above chloropropoxy derivative XXV (R=3—CF$_3$Ph, R$_1$=CF$_3$, B=(CH$_2$)$_3$, halogen=Cl: 0.56 g, 1.2 mM) and piperidine (2 mL, 20.2 mM) in DMF (5 mL) was stirred at reflux for 24 hours. The resulting mixture was concentrated in vacuo, diluted with acetone and purified by column chromatography using EtOAc/MeOH as an eluent to give the title compound as an oil. Oxalic acid (70 mg) was added to a solution of the oil in acetone followed by crystallization of the isolated salt from MeOH/acetone to give the title compound as a solid: mp 172°-174° C.; MS: 519 (MH+). Anal. Calc'd for C$_{25}$H$_{24}$F$_6$N$_4$OS.C$_2$H$_2$O$_4$: C, 49.34; H, 4.31; N, 9.21 Found: C, 49.34; H, 4.12; N, 9.20

EXAMPLE 137

2-[4-[3-(N-Cyclohexylamino)propoxymethyl]-5-(trifluoromethyl)pyrazo-1-yl]-4-(3-trifluoromethylphenyl)thiazole Hemioxalate

The title compound was prepared as described in Example 136 starting with the chloropropoxy derivative from Example 136 (0.76 g, 1.6 mM) and cyclohexylamine (2 mL, 17.4 mM) to give a white solid: mp 130°-132° C.; MS: 533 (MH+). Anal. Calc'd for C$_{24}$H$_{26}$F$_6$N$_4$OS.½(C$_2$H$_2$O$_4$): C, 51.99; H, 4.71; N, 9.70 Found: C, 52.16; H, 5.04; N, 9.46

EXAMPLE 138

2-[4-[3-Aminopropoxymethyl]-5-(trifluoromethyl)-pyrazol-1-yl]-4-(3-trifluoromethylphenyl)thiazole Hydrochloride

The title compound was prepared as described in Example 121 starting with the chloropropoxy derivative from Example 136 (0.8 g, 1.6 mM) to give the hydrochloride salt as a solid: mp 148°-150° C.; MS: 451

(MH+). Anal. Calc'd for $C_{18}H_{16}F_6N_4OS \cdot HCl$: C, 44.41; H, 3.52; N, 11.51. Found: C, 44.23; H, 3.16; N, 11.30

EXAMPLE 139

2-[4-[4-(Amidinobenzylcarbamoyl]-5-(methyl)pyrazol-1-yl]-4-(3-trifluoromethylphenyl)thiazole Hydrochloride A mixture of the pyrazolothiazole acid X (R=3—$CF_3$Ph, $R_1$=$CH_3$: 1.7 g, 4.8 mM) and carbonyldiimidazole (0.9 g, 5.8 mM) in DMF (15 mL) was stirred at room temperature for 1 hour. 4-Aminobenzamidine dihydrochloride (3.0 g, 14.4 mM) was added to the mixture and the reaction was stirred overnight. The resulting mixture was poured into water and a precipitate was collected. The solid was purified by recrystallization from hot methanol to give the title compound as a white solid: mp >260° C.; MS: 471 (MH+). Anal. Calc'd for $C_{22}H_{17}F_3N_6OS \cdot HCl \cdot 0.25 H_2O$: C,51.66; H,3.45; N,16.43 Found: C,51.28; H,3.46; N,16.05

EXAMPLE 140

2-Phenyl-5(4-carboxyphenyl)thiazole

A mixture of 4-trifluoromethylbenzamide (79 mM) and Lawesson's reagent (39 mM) in toluene (200 mL) was heated at reflux for 4 hours under $N_2$. The reaction mixture was cooled and the resulting precipitate was isolated by filtration to give 4-trifluoromethylthiobenzamide as a solid: mp 125° C. (The following general procedure was used to synthesize the various substituted thiobenzamides (Tetrahedron 35,2433, (1979)):

A mixture of an appropriately substituted benzamide (1 meq) and Lawesson's reagent (0.5 meqs) in toluene was heated at reflux for 3–16 hours under $N_2$. The reaction mixture was cooled and the resulting precipitate was isolated by filtration to give the desired thiobenzamide derivative as a solid.

A mixture of freshly prepared 4-carboxyphenacylbromide (13 mM) and thiobenzamide (13 mM) in ethanol (40 mL) was heated at reflux for 2 hours and stirred at room temperature for 72 hours. The resulting mixture was concentrated in vacuo and recrystallized from ether to give the HBr salt of the desired thiazole as a solid.

The following general procedure was used to synthesize the compounds listed in Table 9:

A mixture of freshly prepared substituted phenacylbromide XXVIII (1 meq) and an appropriately substituted thiobenzamide (1 meq) in an appropriate solvent such as ethanol or acetone was heated at reflux for 2–24 hours and allowed to cool to room temperature over 0–72 hours. The resulting mixture was concentrated in vacuo and crystallized from an appropriate solvent such as ether to give the HBr salt of the desired thiazole-benzoic acid XXIX as a solid.

TABLE 9

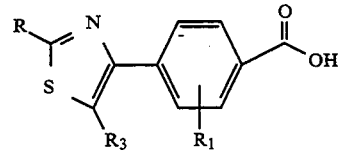

| Ex. # | R | mp °C. |
|---|---|---|
| 140 | Ph | 230–235 |
| 141 | 4-$CF_3$Ph | 275–276 |
| 142 | 4-t-BuPh | 282–283 |
| 143 | 4-$CH_3$Ph | >280 |
| 144 | 4-ClPh | 210(d) |
| 145 | 4-MeOPh | 235–237 |
| 146 | $CH_3$ | >260 |
| 147 | 4-ClPhO$CH_2$ | 147–150 |
| 148 | 4-MeOPhO$CH_2$ | 215–218 |

$R_1$ = H and $R_3$ = H.

EXAMPLE 149

4-[4-(3-Diethylaminopropylcarbamoyl)phenyl]-2-phenylthiazole Monooxalate Hydrate A mixture of the thiazole-benzoic acid XXIX (R=Ph: 1.0 g, 3.6 mM) and carbonyldiimidazole (0.9 g, 5.3 mM) in DMF (8 mL) was stirred for 30 min at room temperature. Diethylaminopropylamine was added to this mixture and the reaction was stirred for 2 hours, followed by the addition of water. The resulting suspension was extracted with several portions of ethyl acetate and the combined organic extracts were dried ($MgSO_4$) and concentrated in vacuo. The residue was treated with hexane and oxalic acid to give the title compound as an oxalate salt: mp 115° C. MS: 394 (MH+). Anal. Calc'd for $C_{23}H_{27}N_3OS \cdot C_2H_2O_4 \cdot H_2O$: C, 59.86; H,6.23; N,8.38 Found: C, 60.20; H,6.16; N,8.80

The following procedure was used in the preparation of the compounds listed 30 in Table 10:

A mixture of the appropriate thiazole-benzoic acid XXIX (1 meq) and carbonyldiimidazole (1.5 meqs) in DMF was stirred for 30 min at room temperature under $N_2$. An appropriately substituted diamine or amino-alcohol was added to this mixture and the reaction was stirred for 1–16 hours, followed by the addition of water. The resulting oil was extracted with several portions of a suitable solvent such as ethyl acetate or methylene chloride and the combined organic extracts were dried ($MgSO_4$) and concentrated in vacuo. Crude XXXIV (A=C(O)NH or C(O)O) was crystallized from a suitable solvent such as ethyl acetate, acetone or ether and isolated as the free base; or treated with a suitable acid such as oxalic acid, succinic acid or conc. HCl in an appropriate solvent such as MeOH, acetone or ether to give the salt of the desired compound. If a precipitate formed from the inital water addition, it was collected by filtration, washed with water and isolated as the free base then converted to its salt.

TABLE 10

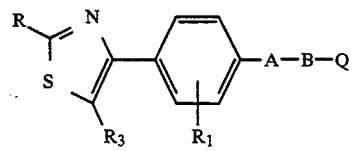

| Compound Ex. # | R | A—B—Q | mp °C. | C | H | N |
|---|---|---|---|---|---|---|
| 149 | Ph | C(O)NH(CH$_2$)$_3$NEt$_2$ | 115–117 | 60.20 | 6.16 | 8.80 |
| 150 | 4-CF$_3$Ph | C(O)NH(CH$_2$)$_3$NEt$_2$ | 168–169 | 56.36 | 5.01 | 7.82 |
| 151 | 4-CH$_3$Ph | C(O)NH(CH$_2$)$_3$NEt$_2$ | 128–131 | 61.69 | 6.05 | 8.33 |
| 152 | 4-ClPh | C(O)NH(CH$_2$)$_3$NEt$_2$ | 122–123 | 56.67 | 5.62 | 8.11 |
| 153 | 4-tBuPh | C(O)NH(CH$_2$)$_3$NEt$_2$ | 155–158 | 64.13 | 6.66 | 7.69 |
| 154 | 4-CH$_3$Ph | C(O)NH(CH$_2$)$_3$NMe$_2$ | 162–164 | 60.36 | 5.58 | 8.99 |
| 155 | 4-CF$_3$Ph | C(O)NH(CH$_2$)$_3$NMe$_2$ | 193–195 | 54.05 | 4.42 | 7.87 |
| 156 | 4-t-BuPh | C(O)NH(CH$_2$)$_3$NMe$_2$ | 175–177 | 62.69 | 6.34 | 8.28 |
| 157 | 4-ClPh | C(O)NH(CH$_2$)$_3$NMe$_2$ | 179–181 | 54.07 | 5.09 | 8.65 |
| 158 | Ph | C(O)NH(CH$_2$)$_2$piperidine | 160–161 | 60.06 | 5.93 | 8.79 |
| 159 | Ph | C(O)NH(CH$_2$)$_3$piperidine | 147–149 | 62.06 | 5.83 | 8.24 |
| 160 | 4-ClPh | C(O)NH(CH$_2$)$_2$piperidine | 161–162 | 56.38 | 5.34 | 7.93 |
| 161 | Ph | C(O)NH(CH$_2$)$_3$imidazole | 163–166 | 58.70 | 4.41 | 11.74 |
| 162 | 4-CF$_3$Ph | C(O)NH(CH$_2$)$_2$piperidine | 172–173 | 54.94 | 4.74 | 7.78 |
| 163 | 4-CH$_3$Ph | C(O)NH(CH$_2$)$_2$piperidine | 165–166 | 60.57 | 5.80 | 8.51 |
| 164 | 4-CF$_3$Ph | C(O)NH(CH$_2$)$_3$pyrrolidinone | 154–158 | 60.91 | 4.56 | 8.77 |
| 165 | 4-CH$_3$Ph | C(O)NH(CH$_2$)$_2$pyrrolidine | 124–127 | 60.38 | 5.53 | 8.13 |
| 166 | 4-ClPh | C(O)NH(CH$_2$)$_2$pyrrolidine | 161–163 | 56.68 | 4.80 | 8.23 |
| 167 | 4-CF$_3$Ph | C(O)NH(CH$_2$)$_2$pyrrolidine | 187–189 | 54.92 | 5.02 | 8.01 |
| 168 | 4-ClPh | C(O)NH(CH$_2$)$_3$pyrrolidine | 168–169 | 56.51 | 5.08 | 7.90 |
| 169 | 4-CF$_3$Ph | C(O)NH(CH$_2$)$_3$pyrrolidine | 140–141 | 54.96 | 4.78 | 7.52 |
| 170 | 4-MePH | C(O)NH(CH$_2$)$_3$pyrrolidinone | 149–152 | 68.58 | 5.68 | 10.01 |
| 171 | 4-ClPh | C(O)NH(CH$_2$)$_2$pyrrolidinone | 139–141 | 62.84 | 4.84 | 9.61 |
| 172 | 4-tBuPh | C(O)NH(CH$_2$)$_2$pyrrolidine | 120–123 | 64.17 | 6.24 | 8.14 |
| 173 | 4-tBuPh | C(O)NH(CH$_2$)$_4$NEt$_2$ | 125–126 | 63.99 | 6.97 | 7.44 |
| 174 | 4-CF$_3$Oh | C(O)NH(CH$_2$)$_2$NMe$_2$ | 90–93 | 52.76 | 4.49 | 8.19 |
| 175 | 4-ClPh | C(O)NH(CH$_2$)$_2$NMe$_2$ | 150–151 | 55.27 | 4.71 | 9.18 |
| 176 | 4-CH$_3$Ph | C(O)NH(CH$_2$)$_2$NEt$_2$ | 160–161 | 61.83 | 5.99 | 8.59 |
| 177 | 4-ClPh | C(O)NH(CH$_2$)$_2$NEt$_2$ | 180–182 | 56.03 | 5.18 | 8.40 |
| 178 | Ph | C(O)NH(CH$_2$)$_3$NMe$_2$ | 173–175 | 59.85 | 5.29 | 9.23 |
| 179 | 4-ClPh | C(O)NH(CH$_2$)$_4$NEt$_2$ | 170–171 | 57.95 | 5.56 | 7.75 |
| 180 | 4-MeOPh | C(O)NH(CH$_2$)$_2$NEt$_2$ | 150–152 | 59.81 | 5.99 | 8.33 |
| 181 | 4-tBuPh | C(O)NH(CH$_2$)$_2$NEt$_2$ | 140–145 | 63.47 | 6.55 | 8.03 |
| 182 | Ph | C(O)NH(CH$_2$)$_2$indolone | 200–205 | 72.19 | 4.88 | 10.29 |
| 183 | 4-MeOPh | C(O)NH(CH$_2$)$_3$NEt$_2$ | 70–80 | 63.08 | 6.31 | 8.82 |
| 184 | 4-tBuPh | C(O)NH(CH$_2$)$_2$NMe$_2$ | 120–125 | 70.50 | 7.16 | 10.11 |
| 185 | Ph | C(O)NH(CH$_2$)$_4$N(iPr)$_2$ | 95–100 | 71.35 | 7.93 | 9.66 |
| 186 | 4-MePh | C(O)NH(CH$_2$)$_2$NMe$_2$ | 125–130 | 68.90 | 6.66 | 11.14 |
| 187 | 4-MeOPh | C(O)NH(CH$_2$)$_3$NMe$_2$ | 120–123 | 66.86 | 6.60 | 10.51 |
| 188 | 4-tBuPh | C(O)NH(CH$_2$)$_2$indoline | 255–257 | 74.08 | 6.16 | 8.29 |
| 189 | 4-CF$_3$Ph | C(O)NH(CH$_2$)$_4$N(iPr)$_2$ | 165–167 | 64.01 | 6.27 | 8.18 |
| 190 | 4-tBuPh | C(O)NH(CH$_2$)$_4$N(iPr)$_2$ | 60–70 | 72.70 | 8.11 | 8.69 |
| 191 | 4-MeOPh | C(O)NH(CH$_2$)$_3$OH | 172–174 | 65.08 | 5.28 | 7.61 |
| 192 | 4-MeOPh | C(O)NH(CH$_2$)$_3$pyrrolidinone | 95–100 | 65.89 | 5.88 | 9.41 |
| 193 | 4-MeOPh | C(O)O(CH$_2$)$_2$NMe$_2$ | 190–192 | 57.46 | 4.95 | 6.08 |
| 194 | Ph | C(O)O(CH$_2$)$_2$NEt$_2$ | 42–44 | 69.54 | 6.71 | 7.17 |
| 195 | 4-MePh | C(O)NH(CH$_2$)$_2$NH$_2$ | >280 | 61.29 | 5.19 | 10.93 |
| 196 | 4-CF$_3$Ph | C(O)NH(CH$_2$)$_2$NH$_2$ | >280 | 53.22 | 3.79 | 9.66 |
| 197 | H | C(O)NH(CH$_2$)$_3$pyrrolidine | 129–131 | 67.45 | 5.61 | 10.39 |
| 198 | 4-MeOPh | C(O)O(CH$_2$)$_2$pyrrolidine | 99–102 | 65.01 | 5.51 | 6.68 |
| 199 | 4-ClPhOCH$_2$ | C(O)NH(CH$_2$)$_3$OH | 176–185 | 59.25 | 4.72 | 6.59 |
| 200 | 4-MeO | C(O)NH(CH$_2$)$_3$OH | 94–96 | 64.98 | 5.54 | 7.39 |
| 201 | 4-ClPhOCH$_2$ | C(O)NH(CH$_2$)$_3$pyrrolidine | 129–135 | 61.01 | 5.16 | 8.56 |
| 202 | CH$_3$ | C(O)NH(CH$_2$)$_3$OH | 81–88 | 60.94 | 5.81 | 10.07 |
| 203 | CH$_3$ | C(O)NH(CH$_2$)$_2$pyrrolidine | 94–95 | 61.98 | 6.31 | 12.39 |
| 204 | 3-MeOPh | C(O)NH-p-C$_6$H$_5$—C(NH)NH$_2$ | 133–136 | 66.27 | 4.5 | 12.97 |
| 205 | CH$_3$ | C(O)NH-p-C$_6$H$_5$—C(NH)NH$_2$ | 119–127 | 60.85 | 5.03 | 15.93 |
| 206 | 4-ClPhOCH$_2$ | C(O)NH(CH$_2$)$_3$NEt$_2$ | 151–157 | 60.31 | 6.12 | 9.12 |
| 207 | 3,4,5-(MeO)$_3$Ph | C(O)NH(CH$_2$)$_3$pyrrolidinone | 142–143 | 61.92 | 6.08 | 8.15 |

R$_3$ = H and R$_1$ = H.

EXAMPLE 208

4-[4-(3-Bromopropylcarbamoyl)phenyl]-2-(4-methylphenyl)thiazole

A mixture of the thiazole-benzoic acid XXIX (R=4-CH$_3$Ph: 5.0 g, 16.9 mM) and carbonyldiimidazole (4.2 g, 25.5 mM) in DMF (50 mL) was stirred for 1 hour at room temperature. 3-Bromopropylamine hydrobromide (18.5 g, 84.5 mM) was added to this mixture and the reaction was stirred for 4 hours, followed by the addition of water. The title compound was isolated from this aqueous mixture as a solid precipitate: mp 175°–177° C. Anal. Calc'd for C$_{20}$H$_{19}$BrN$_2$OS: C, 59.86; H, 6.23; N, 8.38 Found: C, 60.20; H, 6.16; N, 8.80

The following general procedure was used to synthesize the compounds listed in Table 11:

A mixture of an appropriately substituted thiazolebenzoic acid XXIX (1 meq) and carbonyldiimidazole (1.5 meqs) in DMF was stirred for 1 hour at room temperature. The appropriately substituted alkyl bromide such as bromopropanol or bromopropylamine hydrobromide (5 meqs) was added to this mixture and the reaction was stirred for 4 hours, followed by the addition of water. The title compound was isolated from this aqueous mixture as a solid precipitate.

The following general procedure was used to synthesize the compounds listed in Tables 12:

A mixture of the appropriately substituted bromide XXXV (1 meq) and a suitable amine (5-10 meqs) in DMF was stirred for 2-10 hours at room temperature. The mixture was poured into water upon which a precipitate formed and was isolated by filtration. Treatment of the solid with an acid such as conc. hydrochloric acid, conc. hydrobromic acid, oxalic acid, lactic acid, citric acid or succinic acid in a solvent such as methanol, acetone or diethyl ether provided the corresponding salt.

TABLE 11

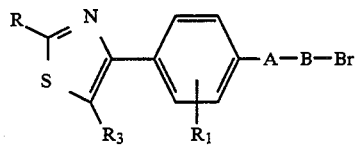

| Compound Ex. # | R | n | A—B—Br | mp °C. | Elemental Analysis C | H | N |
|---|---|---|---|---|---|---|---|
| 208 | 4-CH$_3$Ph | 3 | —C(O)NH(CH$_2$)$_3$Br | 175–177 | 57.40 | 4.48 | 6.86 |
| 209 | 4-CF$_3$Ph | 3 | —C(O)NH(CH$_2$)$_3$Br | 162–164 | 51.07 | 3.06 | 6.28 |

R$_3$ = H and R$_1$ = H.

EXAMPLE 210

TABLE 12

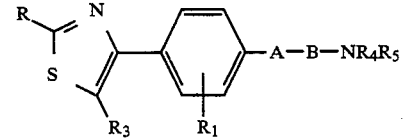

| Compound Ex. # | R | A—B—NR$_4$R$_5$ | mp °C. | Elemental Analysis C | H | N |
|---|---|---|---|---|---|---|
| 210 | 4-CH$_3$ | —C(O)NH(CH$_2$)$_3$piperidine | 202–204 | 63.52 | 5.94 | 8.09 |
| 211 | 4-ClPh | —C(O)NH(CH$_2$)$_3$piperidine | 195–196 | 58.72 | 5.11 | 7.64 |
| 212 | 4-CF$_3$ | —C(O)NH(CH$_2$)$_3$cyclohexylamine | 190–191 | 57.09 | 5.03 | 7.14 |
| 213 | 4-ClPh | —C(O)NH(CH$_2$)$_3$cyclohexylamine | 135–137 | 59.20 | 5.35 | 7.67 |
| 214 | 4-CH$_3$ | —C(O)NH(CH$_2$)$_3$cyclohexylamine | 195–198 | 63.96 | 6.28 | 7.91 |
| 215 | 4-tBu | —C(O)NH(CH$_2$)$_3$cyclohexylamine | 160–161 | 64.83 | 6.83 | 7.48 |
| 216 | H | —C(O)NH(CH$_2$)$_3$pyrrolidine | 155–158 | 61.35 | 5.60 | 8.68 |
| 217 | 4-CH$_3$ | —C(O)NH(CH$_2$)$_3$pyrrolidine | 104–106 | 61.68 | 6.46 | 8.68 |
| 218 | 4-CF$_3$Ph | —C(O)NH(CH$_2$)$_3$NHBu | 154–155 | 57.18 | 5.59 | 6.91 |
| 219 | 4-CH$_3$Ph | —C(O)NH(CH$_2$)$_3$NHBu | 165–167 | 63.24 | 6.35 | 7.61 |
| 220 | H | —C(O)NH(CH$_2$)$_3$NHPr | 190–191 | 60.54 | 5.52 | 8.77 |
| 221 | 4-CF$_3$Ph | —C(O)NH(CH$_2$)$_3$NHPr | 182–184 | 54.83 | 4.66 | 7.66 |
| 222 | 4-tBu | —C(O)NH(CH$_2$)$_3$NHPr | 162–163 | 62.67 | 6.68 | 7.88 |
| 223 | 4-Cl | —C(O)NH(CH$_2$)$_3$NHPr | 206–207 | 57.44 | 5.24 | 8.45 |
| 224 | 4-ClPh | —C(O)NH(CH$_2$)$_3$NHBu | 105–108 | 60.35 | 6.07 | 8.74 |
| 225 | 4-CH$_3$ | —C(O)NH(CH$_2$)$_3$NHPr | 205–207 | 61.31 | 5.82 | 8.65 |
| 226 | 4-MeOPh | —C(O)NH(CH$_2$)$_3$NHBu | 175–180 | 60.79 | 5.97 | 8.11 |
| 227 | 4-MeO | —C(O)NH(CH$_2$)$_3$cyclohexylamine | 161–162 | 61.46 | 6.05 | 7.55 |
| 228 | 3,4,5-MeO | —C(O)NH(CH$_2$)$_3$methylpiperazine | 161–164 | 63.38 | 6.61 | 10.66 |
| 229 | 4-MeOPh | —C(O)NH(CH$_2$)$_3$methylpiperazine | 129–132 | 65.00 | 7.10 | 11.82 |
| 230 | 4-ClPh | —C(O)NH(CH$_2$)$_3$methylpiperazine | 152–154 | 62.99 | 5.92 | 11.99 |

R$_3$ = H and R$_1$ = H.

4-[4-(3-(N-Piperidino)propylcarbamoyl)phenyl]-2-(4-methylphenyl)thiazole Oxalate Hemihydrate A mixture of the bromide XXXV (A=C(O)NH, B=(CH$_2$)$_3$, Q=Br, R=4-CH$_3$Ph: 0.5 g, 1.3 mM) and piperidine (1.1 g, 13 mM) in DMF (3 mL) was stirred for 4 hours at room temperature. The mixture was poured into water upon which a precipitate forms and isolated by filtration. The solid was treated with oxalic acid in acetone to give the oxalate salt of the title compound as a solid: mp 202°–204° C. Anal. Calc'd for C$_{25}$H$_{29}$N$_3$OS.C$_2$H$_2$O$_4$: C, 63.63; H, 6.13; N, 8.25 Found: C, 63.52; H, 5.94; N, 8.09

EXAMPLE 231

4-(3-Trifluoromethyl)phenyl-2-(1-methyl-1H-2-pyrrolyl)-1,3-thiazole Perchlorate

Hydroxylamine hydrochloride (69.2 g, 0.996 mM) was added at room temperature to the pyrrolecarboxaldehyde derivative XXXVII (R$_2$=CH$_3$: 68.1 g, 0.572 mM) and sodium acetate trihydrate (128 g, 0.945 mM) in distilled water (400 mL). The reaction mixture was stirred for 6 hours. 1-Methyl-2-pyrrole hydroxylamine was isolated from this mixture as a solid: mp 128°–32° C.

A mixture of the above oxime derivative XXXVIII (R$_2$=CH$_3$: 35 g, 0.26 mM) and acetic anhydride (130 mL) was heated at reflux for 30 min then cooled to room temperature. The resulting mixture was poured into a suspension of ammonium hydroxide (200 mL) and ice (500 mL), and stirred for 1 hour. The mixture was adjusted to pH 8 by the addition of ammonium hydroxide; followed by another 2 hours of stirring at room temperature. The resulting mixture was extracted with ether, dried (MgSO$_4$), and concentrated in vacuo. The residue was purified by distillation to give 1-methyl-2-pyrrole nitrile as a white oil: MS: 106 (M+); IR (KBR) 2215 cm$^{-1}$.

Hydrogen sulfide was bubbled into a solution of the above nitrile derivative XXXIX (R$_2$=CH$_3$: 3.5 g, 33 mM) and triethylamine (23 mL, 0.165 mM) in pyridine (17.5 mL) for 3 hours at room temperature. The mixture was placed in a dry ice/acetone bath and transferred to a pressure bottle. Additional hydrogen sulfide was bubbled into this flask and stirred at room temperature overnight. Water and methylene chloride were added to the reaction mixture and the organic layer was dried (MgSO$_4$) and concentrated in vacuo. The residue was triturated with water and the resulting solid precipitate was recrystallized from toluene to give 1-methyl-2-pyrrolethioamide as a solid: mp 87°–88° C. 3-Trifluoromethylphenacylbromide (2.72 g, 10.1 mM) was added to a solution of the thioamide derivative XXXX (R$_2$=CH$_3$:1.25 g, 8.92 mM) in ethanol (75 mL), heated at reflux for 2 hours and concentrated in vacuo. The residue was partitioned between ether and 5% NaHCO$_3$, and the organic layer was dried (MgSO$_4$) and concentrated in vacuo. The resulting residue was purified by column chromatography on silica gel using EtOAc/hexanes as an eluent to give the title compound as a light green oil. This oil was treated with perchloric acid and EtOAc to give the title compound as a solid: mp 132°–134 ° C. Anal. Calc'd for C$_{15}$H$_{11}$F$_3$N$_2$.HClO$_4$: C, 44.07; H,2.96; N,6.85 Found: C, 44.14; H,2.70; N,6.72

EXAMPLE 232

5-Carboethoxy-4-phenyl-2-(1-methyl-1H-pyrrol2-yl)-1,3-thiazole

The phenacyl bromide derivative VI (R=Ph, R$_3$=CO$_2$Et (Howk, JACS 54, 282 1932:27.5 g, 0.101 mM) was added to a solution of 1-methyl-2-pyrrolethioamide (12.9 g, 0.92 mM) in ethanol (75 mL), heated at reflux for 2.5 hours and concentrated in vacuo. The residue was partitioned between methylene chloride and K$_2$CO$_3$. The organic layer was separated, extracted with 1N NaOH, dried (MgSO$_4$) and concentrated in vacuo. The resulting residue was purified by column chromatography on silica gel using acetone/hexanes as an eluant; followed by recrystallization from methylcyclohexane to give the title compound as a solid: mp 86°–89 ° C. Anal. Calc'd for C$_{17}$H$_{16}$N$_2$SO$_2$: C, 65.36; H, 5.16; N, 8.97 Found: C,65.35; H, 5.03; N, 8.90.

EXAMPLE 233

2-[2-(3-Aminopropylcarbamoyl)-1-methyl-1H-pyrrol-5-yl]-4-(3-trifluoromethylphenyl)-1,3-thiazole Hemisfumarate Trichloroacetyl chloride (0.14 mL, 1.25 mM) was added to solution of the thiazole-pyrrole XXXXI (R$_7$=CH$_3$, R=3—CF$_3$Ph: 308 mg, 1 mM) in toluene (5 mL) and heated at reflux for 4 hours under argon. More trichloroacetyl chloride (0.7 mL, 0.63 mM) was added to the reaction mixture followed by another 3 hours of heating at reflux. The resulting mixture was concentrated in vacuo to give 2-(1-methyl-5-trichloroacetyl-pyrrol-2-yl)-5-(3-trifluoromethyl)phenyl)thiazole as a brown oil. A solution of the trichloroacetyl derivative XXXXII (R$_2$=CH$_3$, R=3—CF$_3$Ph: 420 mg, 0.92 mM) in acetonitrile (8 mL) was added dropwise to a solution of 1,3-diaminopropane (0.39 mL, 4.63 mM) in acetonitrile (5 mL) at room temperature. The resulting mixture was stirred for 3 hours and concentrated in vacuo. The residue was dissolved in methylene chloride and water and the organic layer was dried and concentrated in vacuo. This residue was treated with fumaric acid and acetonitrile/methanol. The title compound was isolated from this mixture as the hemifumarate salt: mp 205°–208 ° C. Anal. Calc'd for C$_{19}$H$_{19}$F$_3$N$_4$OS.0.5 C$_4$H$_4$O$_4$: C,54.07; H,4.54; N,12.01 Found: C,53.90; H,4.60; N,11.86

The following general procedure was used in the synthesis of the compounds listed in Table 13:

A solution of an appropriately substituted trichloroacetyl derivative XXXXII (1 meq) in acetonitrile was added dropwise to a solution of a suitable diamine or amino-alcohol (4–5 meqs) in acetonitrile at room temperature. The resulting mixture was stirred for 1–3 hours and concentrated in vacuo. The residue was dissolved in methylene chloride and water and the organic layer was dried and concentrated in vacuo. This residue was either recrystallized and isolated as the free base, or treated with suitable acid and isolated as the acid salt.

TABLE 13

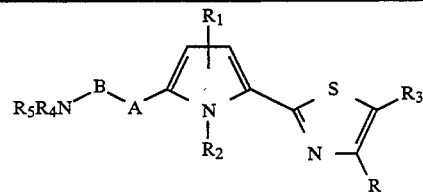

| Compound Ex. # | R | R$_2$ | A—B—NR$_4$R$_5$ | mp °C. | C | H | N |
|---|---|---|---|---|---|---|---|
| 233 | 3-CF$_3$Ph | CH$_3$ | C(O)NH(CH$_2$)$_3$NH$_2$ | 205–08 | 53.90 | 4.60 | 11.86 |
| 234 | 3-CF$_3$Ph | CH$_3$ | C(O)NH(CH$_2$)$_2$NH$_2$ | 205–08 | 53.90 | 4.60 | 11.89 |
| 235 | 3-CF$_3$Ph | CH$_3$ | C(O)NH(CH$_2$)$_4$NH$_2$ | 196-200 | 55.08 | 4.70 | 11.71 |

R$_3$ = H and R$_1$ = H.

EXAMPLE 236

2-[2-(4-Cyclohexylaminopropylcarbamoyl)-1-methyl-1H-pyrrol-5-yl]-4(3-trifluoromethylphenyl)thiazole Sodium cyanoborohydride (583 mg, 8.82 mM) was added to a solution of 2-(1-methyl-5-(3-aminopropyl)-carbamoyl)pyrrol-2-yl )-5-( 3-trifluoromethyl)phenyl)-thiazole (3 g, 7.35 mM) and cyclohexanone (721 mg, 7.35 mM) in methanol (10 mL) and stirred overnight at room temperature under argon. The resulting mixture was adjusted to pH 1 with 3N HCl and stirred for 2–3 hours. The mixture was then treated with 3N NaOH and extracted with methylene chloride. The combined organic extracts were dried ($MgSO_4$) and concentrated in vacuo. The residue was purified by column chromatography on silica gel and recrystallization from acetonitrile to give the title compound as a solid: mp 120°–123° C. 15 Anal. Calc'd for $C_{25}H_{29}F_3N_4OS$: C, 61.21; H,5.96; N,11.42 Found: C, 61.36; H,6.07; N,11.55

EXAMPLE 237

2-[2-(4-Aminopropylcarbamoyl)-1-methyl-1H-pyrrol-5-yl]-4-phenyl-1,3-thiazole-5-carboxylic acid monohydrochloride monohydrate Trichloroacetyl chloride (2.9 mL, 26 mM) was added to solution of thiazole XXXXI ($R_3=CO_2Et$, $R_2=CH_3$, R=Ph: 3.0 g, 9.62 mM) in toluene (30 mL) and heated at reflux for 48 hours under argon. The resulting mixture was washed with 5% $NaHCO_3$ (aq) and the organic layer was dried ($MgSO_4$) filtered and concentrated in vacuo. The residue was purified by column chromatography, using ethyl acetate/hexane as an eluent and crystallized from methylcyclohexane to give the trichloroacetyl derivative XXXXI ($R_3=CO_2Et$, $R_2=CH_3$, R=Ph) as a solid. Anal. Calc'd for $C_{19}H_{15}Cl_3N_2O_3S$: C,49.85; H,3.30; N,6.12 Found: C,50.86; H,3.48; N,6.15

The amide derivative XXXXIII can be prepared as described above starting with the trichloroacetyl derivative XXXXII ($R_3=CO_2Et$, $R_2=CH_3$, R=Ph: 2.5 g, 3.47 mM) and 1,3-diaminopropylamine (2.28 mL, 27.35 mM) in $CH_3CN$ (100 mL). The desired amide derivative XXXXIII ($R_3=CO_2Et$, $R_2=CH_3$, R=Ph, $R_4$ and $R_5=H$, $B=(CH_2)_3$) was purified by chromatography, converted to the HCl salt and isolated as such. NaOH (5 g 0.13M) was added to a solution of amide XXXXIII ($R_3=CO_2Et$, $R_2=CH_3$, R=Ph, $R_4$ and $R_5=H$, $B=(CH_2)_3$: 1.0 g, 2.42 mM in ethanol and heated to reflux for 20 min. The reaction mixture was concentrated in vacuo, dissolved in water, acidified with 3N HCl until the pH of the mixture was 7.5 and concentrated in vacuo once again. The residue was washed with a small portion of water and suspended in 3N HCl. The title compound was isolated from this mixture as the hydrochloride salt: mp 209°–210° C.

BIOLOGICAL ASSAYS

Platelet Aggregation Inhibition Activity

The compounds of the invention as identified above and synthesized in accordance with the representative examples were evaluated for platelet aggregation inhibition activity in accordance with the following procedure. The percentage of platelet aggregation is calculated as an increase in light transmission of drug treated platelet concentrate versus control treated platelet concentrate. Blood is obtained from drug free, normal donors into tubes containing 0.13M sodium citrate (two sources are routinely used: platelet concentrate obtained from Biological Specialty Corp., Lansdale, Pa. or whole blood obtained from donors). Platelet rich plasma (PRP) is collected by centrifugation of the concentrate or whole blood at $130 \times g$ for 15 minutes at 25° C. The PRP (5 mL) is gel filtered through Sepharose 2B (bed volume 50 mL), and the platelet count is adjusted to $2 \times 10^7$ platelets per sample. The following constituents are added to a siliconized cuvette: 250 μL of the concentrated platelet filtrate, 100 μL of Tyrode's buffer (0.14M NaCl, 0.0027M KCl, 0.012M $NaHCO_3$, 0.76 mM $Na_2HPO_4$, 0.0055M glucose and 2 mg/mL BSA pH 7.4), 50 μL of 2 mM calcium and test drug (50 mL).

Aggregation is monitored in a dual channel Chronolog Aggregometer for three minutes following the addition of agonist (thrombin 50 μL of 1 unit/mL, or ADP 50 μL of 100 μM). The final assay volume is 500 μL. The reaction takes place at 37° C. The peak aggregation response is calculated as the increase in light transmission units over a three minute period. The difference of the increase in light transmission between control and drug treated platelets is then expressed as a percent of the nondrug treated controls. The percentage of inhibition of platelet aggregation of certain selected compounds is displayed in Tables below. A percentage increase in light transmission indicates platelet aggregation inhibition activity for the tested compound. A concentration of $IC_{50}$ or concentration of the compound in μM at which the increase in light transmission equals 50% is provided in the "Aggregation" column. For some compounds the percentage increase in light is indicated as greater than 50% in the Aggregation column for a given concentration.

Fibrinogen Binding

The compounds of the invention as identified above are evaluated for platelet aggregation inhibition activity as indicated by the percentage of nonaggregated platelets which are available for binding in accordance with the following procedure.

$^{125}I$-fibrinogen binding to activated platelets is a modification of the procedure described by Bennett et al., 1988. Briefly, 40 mL of PRP (obtained from Biological Specialty Corp., Lansdale, Pa.) are centrifuged at $120 \times g$ to remove contaminating red cells. Aspirin (50 μM) is added and the PRP is incubated at 37° C. for 20 minutes. The pH of the PRP is adjusted to 6.5 with 3.8% sodium citrate and 0.9 μM of PGE1 is added. Platelets are concentrated by a $300 \times g$ centrifugation (10 minutes) and the pellet is resuspended in 4 mL. of Tyrode's buffer. The platelet suspension (4 mL) is gel-filtered through a Sepharose-2B column (50 mL bed volume). The platelet count is adjusted to $1 \times 10^8$ platelets per 200 mL. The binding reaction is performed in polystyrene tubes (final volume 500 mL). Reagents are added in the following order: 80 mL of Tyrode's buffer, 50 mL of $CaCl_2$ (final concentration (f.c.) 0.2 μM) and 50 mL of thrombin (f.c. 0.1 unit/mL). The platelet suspension is then added and the mixture is allowed to incubate at room temperature for 2 minutes. Hirudin (50 mL, f.c. 0.5 unit/mL) is immediately added to prevent the catalytic activity of thrombin. Various concentrations of the compound to be tested (50 mL) with the competing radioligand $^{125}I$-fibrinogen (f.c. of 0.15 μM) are added. The mixture is incubated for 10 minutes at room temperature. To terminate the binding reaction the platelets are sedimented ($10,000 \times g$ for 3 minutes) through silicone oil (3:1 hi-phenol 550/methyl silicone 200, W. F. Nye, Inc., New Bedford, Mass.), in an Eppendorf centrifuge.

The tips of the centrifuge tubes containing the pelleted platelets are cut off and counted for $^{125}$I-fibrinogen associated with the stimulated platelets. The amount of platelet radioactivity measured in the presence of nonlabeled fibrinogen (4 mg/mL) is considered the nonspecific binding. All samples are repeated in triplicate.

Data are expressed as a percent at concentrations of 30 $\mu$M of specifically bound $^{125}$I-fibrinogen to the platelets in Tables 14–16 below. Positive percentages of fibrinogen binding indicates higher activity for inhibiting platelet aggregation since only non-aggregated or free platelets are available for fibrinogen binding. Alternatively, a concentration is provided in lieu of a percentage to indicate the IC$_{50}$ of concentration of compound which provides 50% fibrinogen binding.

TABLE 14

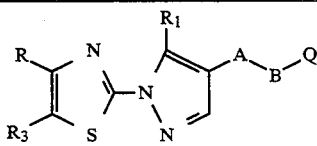

| Ex # | Binding | Aggregation | Ex # | Binding | Aggregation |
|---|---|---|---|---|---|
| 34 | 6 μM | 50 μM | 61 | 61% | 11.5 μM |
| 35 | 64% | 75 μM | 62 | 8.3 μM | 4.6 μM |
| 36 | 50 μM | 50 μM | 89 | 10 μM | 13 μM |
| 37 | 4 μM | 15 μM | 90 | 14 μM | 15 μM |
| 38 | 75 μM | 56 μM | 91 | 10 μM | 5 μM |
| 39 | 16 μM | 30 μM | 92 | 64% | 10 μM |
| 40 | 65 μM | 30 μM | 93 | 25% | 30 μM |
| 41 | 57% | 30 μM | 94 | 50% | 40 μM |
| 43 | 70 μM | 6 μM | 95 | 7% | 30 μM |
| 45 | 8.5 μM | 45 μM | 96 | 56% | 3.5 μM |
| 46 | 11.3 μM | 2.7 μM | 97 | — | 10 μM |
| 47 | — | 5.6 μM | 99 | 34% | 30 μM |
| 48 | 42% | 50 μM | 100 | 21% | 30 μM |
| 49 | 25% | 60 μM | 101 | 40% | 15 μM |
| 50 | 50 μM | 30 μM | 102 | 25 μM | 6 μM |
| 51 | 14% | 30 μM | 105 | 44 μM | 8 μM |
| 52 | 68% | 6 μM | 106 | 85% | 30 μM |
| 54 | 53% | 10 μM | 107 | 100% | 5 μM |
| 55 | 12% | 30 μM | 108 | 100% | 20 μM |
| 56 | 100% | 4 μM | 109 | 100% | 6 μM |
| 57 | 100% | 7 μM | 111 | 15 μM | 15 μM |
| 112 | 91% | 5 μM | 123 | 17 μM | 17 μM |
| 113 | 10 μM | 3.1 μM | 124 | 5.5 μM | 3.2 μM |
| 114 | 10 μM | 7 μM | 128 | 17.5 μM | 118 μM |
| 120 | 23 μM | 13 μM | 136 | 17 μM | 21 μM |
| 121 | 15 μM | 6 μM | 132 | 39% | 7 μM |
| 122 | 10 μM | 14.7 μM | 138 | 69% | 2.1 μM |

TABLE 15

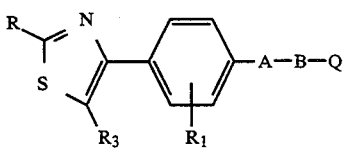

| Ex. # | Binding | Aggregation | Ex. # | Binding | Aggregation |
|---|---|---|---|---|---|
| 150 | 4.4 μM | 5.0 μM | 189 | 100% (30 μM) | 86% @ 20 μM |
| 151 | 19 μM | 16.7 μM | 196 | 6 μM | 3.7 μM |
| 153 | 4.3 μM | 15.3 μM | 206 | — | 5.1 μM |
| 154 | 10 μM | 7.2 μM | 209 | 7.8 μM | 5.5 μM |
| 158 | 5.2 μM | 8.7 μM | 211 | 3.4 μM | 5 μM |
| 156 | 12 μM | 14.2 μM | 213 | 9.2 μM | 10 μM |
| 170 | 10.8 μM | 90% @ 20 μM | 218 | 100% (30 μM) | 90% @ 20 μM |

TABLE 15-continued

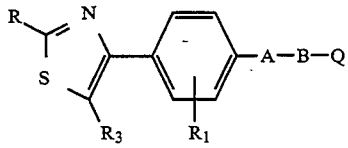

| Ex. # | Binding | Aggregation | Ex. # | Binding | Aggregation |
|---|---|---|---|---|---|
| 174 | 1.8 μM | 85% @ 20 μM | 221 | 5.8 μM | 85% @ 20 μM |
| 177 | 8.4 μM | 12.8 μM | 224 | 3.3 μM | 6.1 μM |
| 176 | 2.5 μM | 4 μM | 226 | 4.3 μM | 3.8 μM |
| 179 | 2.7 μM | 5.8 μM | 229 | 3.9 μM | 11.3 μM |
| 181 | 100% | 85% @ 20 μM | 230 | 6.6 μM | 4.0 μM |
| 187 | 100% (30 μM) | 89% @ 20 μM | | | |

TABLE 16

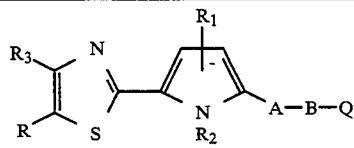

| Ex. # | Binding | Aggregation |
|---|---|---|
| 233 | 100% at 50 μM | — |
| 234 | 100% at 50 μM | — |
| 235 | 100% at 50 μM | — |
| 236 | 13.5 μM | — |
| 237 | — | 68% at 50 μM |

The above test results demonstrate the utility of the compounds of the invention for inhibiting platelet aggregation. The scope of the present invention is not limited by the description, examples and suggested uses described herein and modifications can be made without departing from the spirit of the invention. For example, additional medicaments or active components may be used in combination with the compounds of the invention or two or more compounds of the invention may be used in combination in a pharmaceutical composition. Further, the novel compounds of the invention may have other uses in addition to those described herein.

Pharmaceutical compositions containing compounds of the invention may comprise the compound of the present invention and a pharmaceutically acceptable carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methylcellulose, sodium carboxymethylcellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8 Chapters 76-93, "Pharmaceutical Preparations and Their Manufacture", pp. 1409-1677 (1985).

In therapeutic use as inhibitors of platelet aggregation and/or fibrinogen binding, the compounds utilized in the methods of this invention may be administered to a patient either orally or parenterally at dosage levels from about 1-100 mg/kg and preferably about 3-10 mg/kg of body weight per day. The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

Applications of the compounds, compositions, and methods of the present invention for medical or pharmaceutical uses can be accomplished by any clinical, medical, and pharmaceutical methods and techniques as are presently or prospectively known to those skilled in the art. Thus it is intended that the present invention cover any modifications and variations of this invention provided that they come within the scope of the appended claims and their equivalents.

What is claimed is:

1. A compound of the formula:

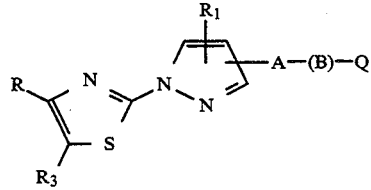

I wherein
R and $R_3$ are the same or different and are selected from hydrogen, hydroxy, carboxy, alkylcarboxy ($C_1$-$C_4$), alkyl ($C_1$-$C_8$), trifluoromethyl, halogen, phenyl or substituted phenyl, where the phenyl substituents are selected from the group consisting of cyano, nitro, trifluoromethyl, carboxy, amino, carboxamido, tosyl, halogen, alkyl ($C_1$-$C_4$), carboalkoxy ($C_1$-$C_4$), and alkoxy ($C_1$-$C_4$), or heteroaryl wherein the heteroaryl contains 1-4 heteroatoms selected from nitrogen or sulfur or R and $R_3$ are taken together to form a ring, except for formula III, selected from benzene or substituted benzene wherein such substituents are selected from the group consisting of cyano, nitro, trifluoromethyl, carboxy, amino, carboxamido, halogen, alkylcarboxy, alkyl or alkoxy wherein the halogen, alkoxy, alkylcarboxy and alkyl groups are as defined above;

$R_1$ is selected from the group consisting of hydrogen, halogen, hydroxy, carboxy, alkylcarboxy ($C_1$-$C_4$), alkyl ($C_1$-$C_5$), trifluoromethyl, phenyl or substituted phenyl wherein where the phenyl substituents are selected from the group consisting of cyano, nitro, trifluoromethyl, carboxy, amino, carboxamido, tosyl, halogen, alkyl ($C_1$-$C_4$), carboalkoxy ($C_1$-$C_4$), and alkoxy ($C_1$-$C_4$);

$R_2$ is hydrogen or alkyl ($C_1$-$C_5$);

A is selected from the group consisting of carbonyl, carboxyl, carboxamido, amido, oxymethyl, aminomethyl, or methylene;

B is selected from alkyl ($C_1$-$C_9$), branched alkyl ($C_1$-$C_9$), phenyl or aralkyl ($C_1$-$C_5$); and Q is selected from hydroxy, alkoxy ($C_1$-$C_5$), halogen, cyano, carboxy, alkoxycarbonyl ($C_1$-$C_5$), or $NR_4R_5$ where $R_4$ and $R_5$ are independently selected from the group consisting of hydrogen, alkyl ($C_1$-$C_5$), cycloalkyl ($C_3$-$C_8$), or $NR_4R_5$ is taken together to form a heterocyclic ring selected from piperidine, pyrrolidine, pyrrolidinone, piperidinone, phthalimide, imidazole, piperazine, substituted piperazine or morpholine and their benzo fused analogues selected from 2,6-dihydro-isoindole and benzimidazole and any N-oxides thereof selected from 2-oxo-2,6-dihydro-isoindole or $NR_4R_5$ is guanidine, urea, thiourea, hydrazine, amidine, or substituted amidine wherein the substituents are selected from the group consisting of alkyl ($C_1$-$C_4$), hydroxyl and amino; and pharmaceutically acceptable salts thereof.

2. A compound according to claim 1 wherein:
the aryl and substituted aryl are phenyl and substituted phenyl and the substituents are as defined above for the substituted aryl; and
the heteroaryl comprises a nitrogen or sulfur or both or is selected from the group consisting of thiophene, imidazole and pyridine.

3. A compound according to claim 2 wherein:
R and $R_3$ are the same or different and are selected from hydrogen, halogen or substituted phenyl, wherein the phenyl substituents are selected from the group consisting of trifluoromethyl, halogen, alkyl ($C_1$-$C_4$) or alkoxy ($C_1$-$C_4$);
$R_1$ and $R_2$ are the same or different and are selected from the group consisting of hydrogen, alkyl ($C_1$-$C_4$) or trifluoromethyl;
A is carboxamido, aminomethyl or oxymethyl;
B is alkyl ($C_1$-$C_9$); and
Q is selected from hydroxy or $NR_4R_5$, where $R_4$ and $R_5$ are independently selected from the group consisting of hydrogen, alkyl ($C_1$-$C_5$), cycloalkyl ($C_3$-$C_8$), or $NR_4R_5$ is taken together to form a heterocyclic ring selected from the group consisting of piperazine, substituted piperazine, pyrrolidinone, and imidazole or NR4R5 is a guanidine, amidine or substituted amidine.

4. A compound according to claim 1 of the formula:

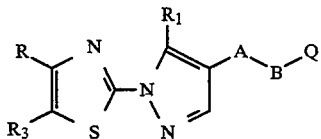

wherein R is 3—CF3Ph, 3-ClPh or 4-CH3OPh; R3 is H, Br, CO2H; and R1 is CF3, CH3 or H.

5. A compound according to claim 4 of the formula:

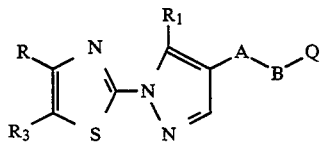

wherein A is C(O)NH, CH2O or CH2NH and B is alkyl (C1-7).

6. A compound according to claim 5 of the formula:

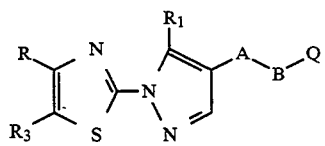

wherein Q is hydroxy or NH2, NEt2, NMe2, NHBu, NHisopropyl, NHcyclohexyl, piperazine, methyl piperazine, pyrrolidinone, imidazole, morpholine, guanidine, amidine or substituted amidine.

7. A compound according to claim 6 selected from the group consisting of:
2-[4-[2-(N,N-Diethylamino)ethylcarbamoyl]-5-(trifluoromethyl)pyrazol-1-yl]-4-(3-trifluoromethylphenyl) thiazole; 2-[4-[2-(N,N-Dimethylamino)ethyl-carbamoyl]-5-(trifluoromethyl)pyrazol-1-yl]-4-(3-trifluorometylphenyl) thiazole; 2-[4-[3-(N,N-Diethylamino)propylcarbamoyl]-5-(trifluoromethyl)-pyrazol-1-yl]-4-(3-trifluoromethylphenyl) thiazole; 2-[4-[3-(N,N-Diethylamino)propylcarbamoyl]pyrazol-1-yl]-4-(3-trifluoromethylphenyl) thiazole; 5-Bromo-2-[4-[3-(N,N-diethylamino)-propylcarbamoyl]-5-(trifluoromethyl)pyrazol-1-yl]-4-(3-trifluoromethylphenyl) thiazole; 2-[4-[3-(N,N-Dimethylamino)propylcarbamoyl]-5-(trifluoromethyl)pyrazol-1-yl]-4-(3-trifluoromethylphenyl) thiazole; 2-[4-[3-(Cyclohexylamino)-propylcarbamoyl]-5-(trifluoromethyl)-pyrazol-1-yl]-4-(3-trifluoromethylphenyl) thiazole; 2-[4-[3-(N-Piperidino)propylcarbamoyl]-5-(trifluoromethyl)-pyrazol-1-yl]-4-(3-trifluoromethylphenyl) thiazole; 2-[4-[4-(N,N-Dimethylamino)butylcarbamoyl]-5-(trifluoromethyl)pyrazol-1-yl]-4-(3-trifluoromethylphenyl) thiazole; 2-[4-[3-(N-Imidazo)-propylcarbamoyl]-5-(trifluoromethyl)-pyrazol-1-yl]-4-(3-trifluoromethylphenyl) thiazole; 2-[4-[4-(N,N-Diethylamino)butylcarbamoyl]-5-(trifluoromethyl)pyrazol-1-yl]-4-(3-trifluoromethylphenyl) thiazole; 2-[4-[7-(N,N-Diethylamino)heptylcarbamoyl]-5-(trifluoromethyl)-pyrazol-1-yl]-4-(3-trifluoromethylphenyl) thiazole; 2-[4-[2-Aminoethylcarbamoyl]-5-(trifluoromethyl)pyrazol-1-yl]-4-(3-trifluoromethylphenyl)thiazole; 2-[4-[3-Aminopropylcarbamoyl]-5-(trifluoromethyl)-pyrazol-1-yl]-4-(3-trifluoromethylphenyl) thiazole; 2-[4-[4-Aminobutylcarbamoyl]-5-(trifluoromethyl)-pyrazol-1-yl]-4-(3-trifluoromethylphenyl) thiazole; 2-[4-[3-Aminopropoxymethyl]-5-(trifluoromethyl)pyrazol-1-yl]-4-(3-trifluoromethylphenyl)thiazole; 2-[4-[3-(N-Morpholino)propylcarbamoyl]-5-(trifluoromethyl)pyrazol-1-yl]-4-(4-methoxyphenyl) thiazole or 2-[4-[3-(2-Oxo-1-pyrrolidinyl)-propyl-carbamoyl-5-(trifluoromethyl)-pyrazol-1-yl]-4-(4-methoxyphenyl) thiazole.

8. A compound according to claim 6 of the formula:
2-[4-(3-Guanidinopropylcarbamoyl)-5-(trifluoromethyl)pyrazol-1-yl]-4-(3-trifluoromethylphenyl)-thiazole; 2-[4-(3-Amidinopropylcarbamoyl)-5-(trifluoromethyl)pyrazol-1-yl]-4-(3-trifluoromethylphenyl)thiazole; or 2-[4-[3(N,N-Dimethylforamidinyl)-propylcarbamoyl]-5-(trifluoromethyl)pyrazol-1-yl]-4-(3-trifluoromethyl-phenyl)-thiazole.

9. A method of treating reperfusion thrombosis injury in a patient comprising the step of administering to the plasma of a patient an amount of a compound of claim 1 effective to inhibit platelet aggegation.

10. A method of treating reperfusion thrombosis injury in a patient comprising the step of administering to the plasma of a patient an amount of a compound of claim 2 effective to inhibit platelet aggegation.

11. A method of treating reperfusion thrombosis injury in a patient comprising the step of administering to the plasma of a patient an amount of a compound of claim 3 effective to inhibit platelet aggegation.

12. A pharmaceutical composition comprising one or more compounds of claim 1 and a pharmaceutically inert carrier.

13. A pharmaceutical composition comprising one or more compounds of claim 2 and a pharmaceutically inert carrier.

14. A pharmaceutical composition comprising one or more compounds of claim 3 in a pharmaceutically inert carrier.

* * * * *